US009212398B2

(12) United States Patent
You

(10) Patent No.: US 9,212,398 B2
(45) Date of Patent: Dec. 15, 2015

(54) CROSS PRIMING AMPLIFICATION OF TARGET NUCLEIC ACIDS

(76) Inventor: Qimin You, Hangzhou (CN)

(*) Notice: Subject to any disclaimer, the term of this patent is extended or adjusted under 35 U.S.C. 154(b) by 232 days.

(21) Appl. No.: 13/135,258

(22) Filed: Jun. 30, 2011

(65) Prior Publication Data

US 2014/0093877 A1    Apr. 3, 2014

Related U.S. Application Data

(60) Provisional application No. 61/398,798, filed on Jul. 1, 2010.

(51) Int. Cl.
*C12Q 1/68* (2006.01)

(52) U.S. Cl.
CPC .............. *C12Q 1/689* (2013.01); *C12Q 1/6853* (2013.01); *C12Q 1/6888* (2013.01)

(58) Field of Classification Search
None
See application file for complete search history.

(56) References Cited

U.S. PATENT DOCUMENTS

2009/0181388 A1 *   7/2009   You et al. ................... 435/6

OTHER PUBLICATIONS

Mothershed et al. (2006) Clinica Chimica Acta vol. 363 pp. 206-220.*
Schweitzer et al. (2001) Current opinion in Bitotechnol. vol. 12:pp. 21-27.*

* cited by examiner

*Primary Examiner* — Suchira Pande
(74) *Attorney, Agent, or Firm* — G Kenneth Smith

(57) ABSTRACT

The present invention relates to methods of amplification of nucleic acid sequences; more particularly, it relates to methods of amplifying target sequences by utilizing cross priming isothermal amplification. The present invention relates to methods of marking the amplification target sequence during the amplification reaction and rapid detection of the target sequence. The present invention also relates to reagent kits for rapid nucleic acid diagnosis and the nucleic acid detection of pathogenic microorganisms such as bacteria, viruses, as well as to diagnoses related to human genetic diseases.

4 Claims, 28 Drawing Sheets

Figure 11B:
Target sequence, primer locations and primer design

```
TB IS6110 target sequence
GCCATCGTGGAAGCGACCCGCCAGCCCAGGATCCTGCGACGTAGGCGCTCGGTGACAA
AGGCCACGTAGGCGAACCCTGCCCAGGTCGACACATAGGTGAGGTCTGCTAACCACA
GCCGGTTAGGTGCTGGTGGTCCGAAGCGGCGCTGGACGAGATCGGCGGGACGGGCTGT    SEQ ID 16
                                 Xba I
1s. 5-TAGCAGACCTCACCTATGTGTCTTCTAGATCGGTGACAAAGGCCACGT  SEQID 11
2a. 5-TAGCAGACCTCACCTATGTGTC   SEQ ID 9
3a. 5-CTGGGCAGGGTTCGCCT  SEQ ID 10
4s. 5-GCCATCGTGGAAGCGA   SEQ ID 17
5a. 5-ACAGCCCGTCCCGCCGAT SEQ ID 8
```

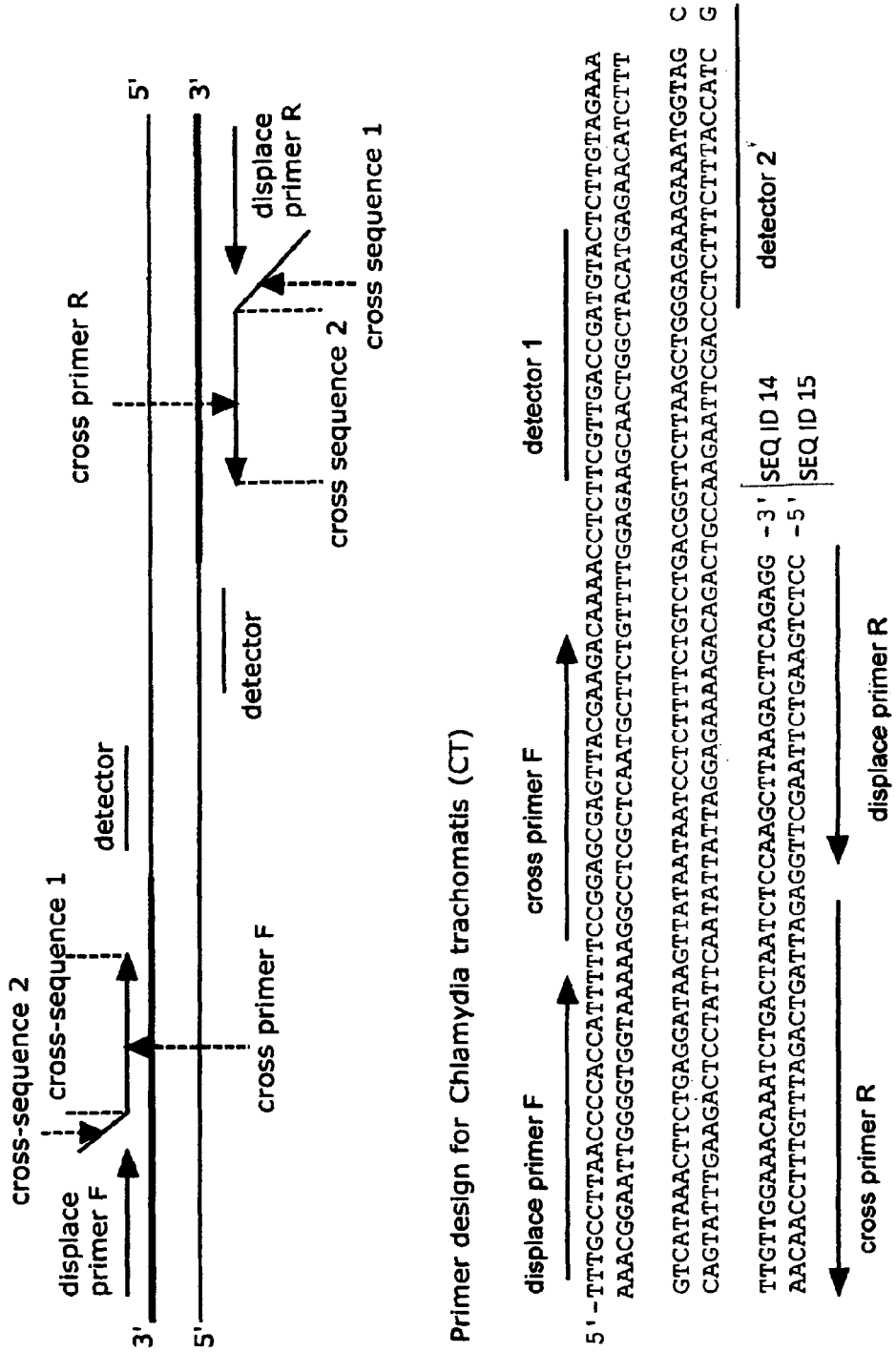

FIGURE 2 (CONT'D)

Displace primer F: 5'-TTTGCCTTAACCCCACCAT-3' (SEQ ID 1)

Displace primer R: 5'-CCTCTGAAGTCCTTAAGCTTG-3' (SEQ ID 2)

Cross primer F: 5'-ATTAGTCAGATTGTTTCCAACTTCCGGAGCGAGTTACGAAGA-3' (SEQ ID3)

Cross primer R: 5'-TCCGGGAGCGAGTTACGAAGATATTAGTCAGATTGTTTCCAAC-3' (SEQ ID 4)

Detector 1: 5'-TACAAGAGTACATCGGTCAA-3' (SEQ ID 5)

Detector 2: 5'-GGGAGAAGAAATGGTAGC-3' (SEQ ID 6)

GENERATION OF DEFINED 5' AND 3' ENDS; GENERATION OF CROSS PRIMING SITES AT BOTH ENDS

**CROSS PRIMING AMPLIFICATION
MECHANISM OF DETECTION**

TB 1S6110 TARGET SEQUENCE

GCCATCGTGGAAGGACCCGCCAGCCAGGATCCTGCGACGTAGGCGCTCGGTGACAAAGGCCACGTAGGCGAACCTGCCCAGGTCGACACATAGGTGAGGT
CTGCTAACCACAGCCGGTAGGTGCTGGTGGTCCGAAGCGGCGCTGGACGAGATCGGCGGGACGGGACGGGCTGT (SEQ ID 16)

Xba I

1s:    5'-TAGCAGACCTCACCTATGTGTCTCTAGATCGGTGACAAAGGCCACGT (SEQ ID 11)

2a:    5'-TAGCAGACCTCACCTATGTGTC (SEQ ID 9)

3a:    5'-CTGGGCAGGGTTCGCCT (SEQ ID 10)

4s:    5'-GCCATCGTGGAAGCGA (SEQ ID 17)

5a:    5'-ACAGCCCGTCCCGCCGAT (SEQ ID 8)

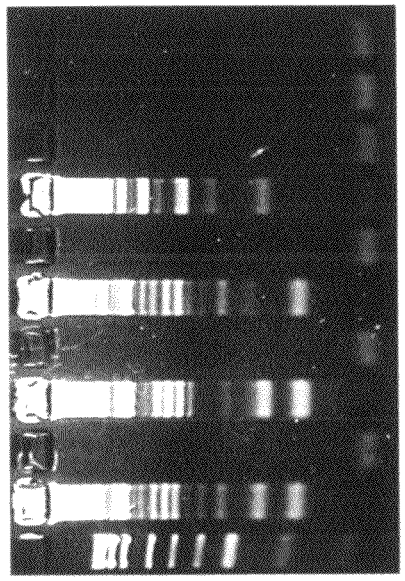
Figure 8C: Amplification products with different primer combinations

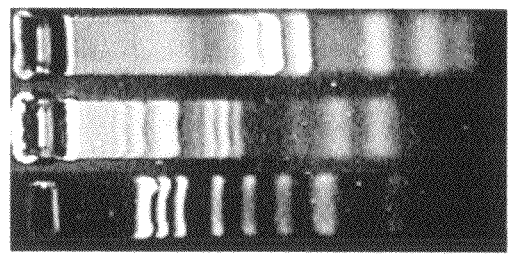
Figure 8D: Restriction Digest of Amplification Products

Sequence analysis of amplification products

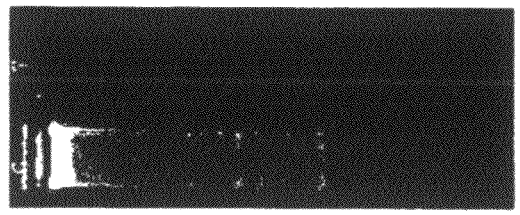
Figure 9B: Gel image of heterozygous amplification products

Figure 10A: Mechanism of double primer crossing amplification
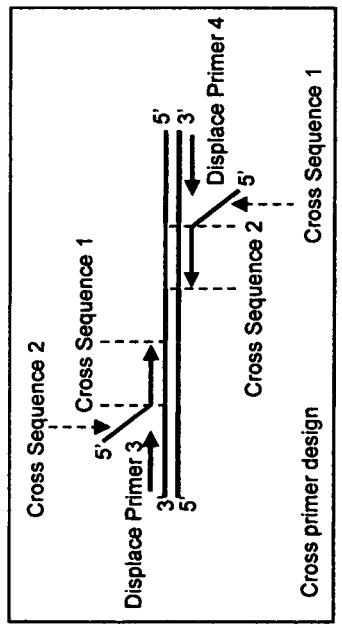
HPV target sequence and CPA primer design, displacement primers not shown. The primer tags were designed for identification of each primer location in the sequenced amplification product.

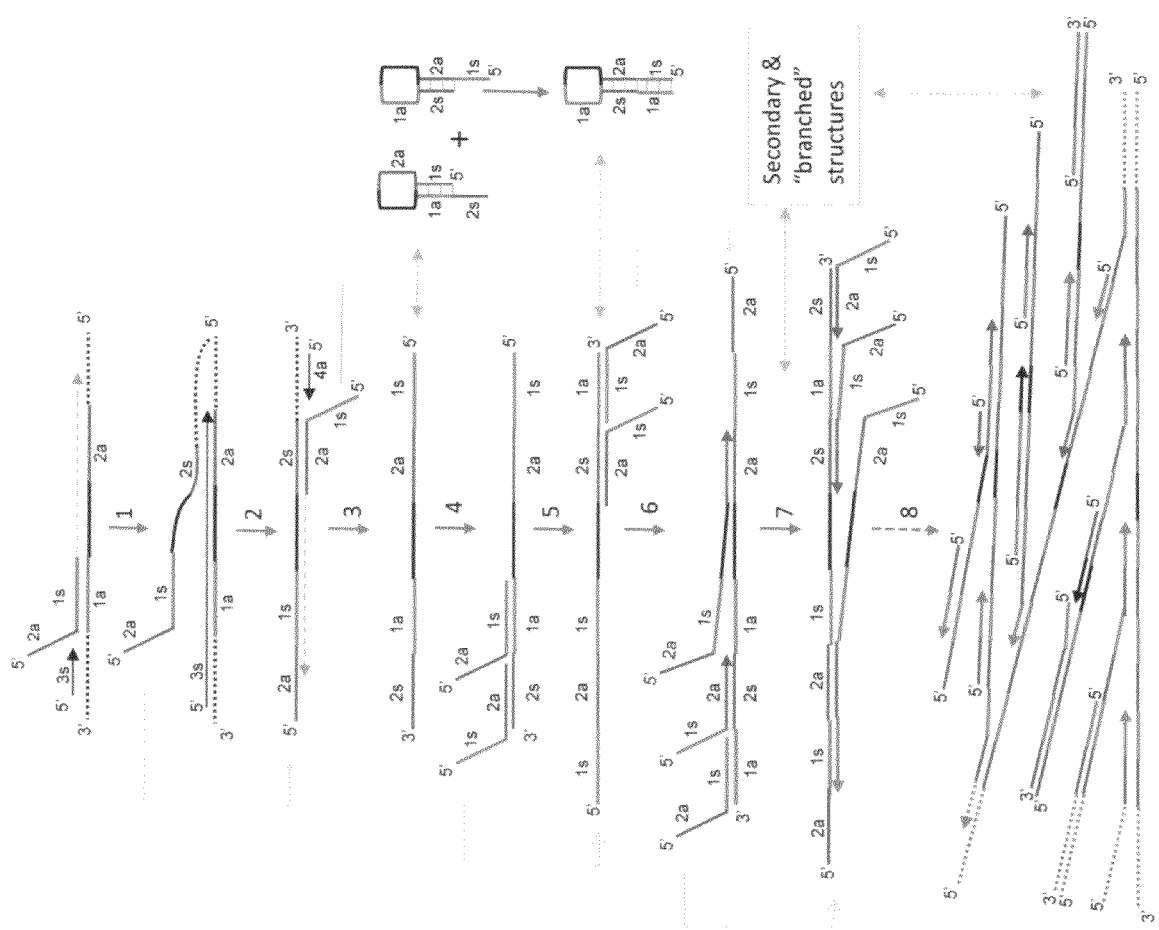
Figure 10B.: Schematic of Cross Priming Amplification (double crossing)

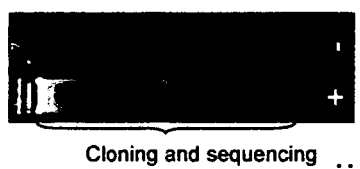
Figure 10C:
Gel image of heterozygous amplification products
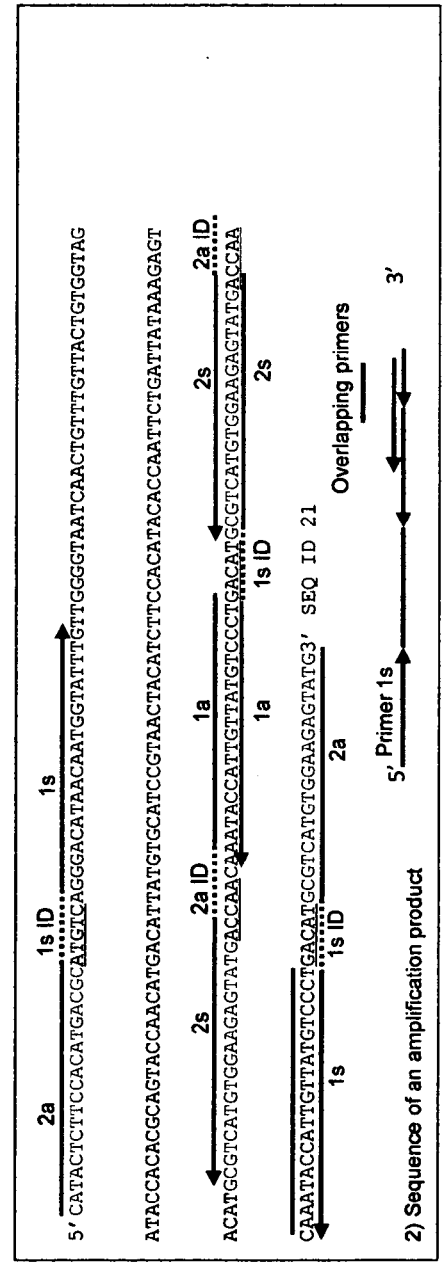
Figure 10D: Sequencing of an amplification product

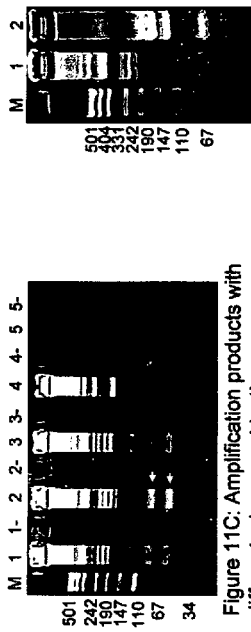

Figure 11B:
Target sequence, primer locations and primer design

```
TB IS6110 target sequence
GCCATCGTGGAAGCGACCCGCCAGCCCAGGATCCTGCGAGCGTAGGCGCTCGGTGACAA
AGCCACGTAGGCGAACCCTGCCCAGGTCGACATAGGTGAGGTCTGCTAACCACA
GCCGGTTAGGTGCTGGTGGTCCGAAGCGGCGCTGACGAGATCGGCGGAGGGGCTGT      SEQ ID 16
                                   XbaI
1s. 5-TAGCAGAGACCTCACCTATGTCTTCTAGATCGGTGACAAAGGCCACGT  SEQ ID 11
2a. 5-TAGCAGAGACCTCACCTATGTGTC                          SEQ ID 9
3a. 5-CTGGGCAAGGTTCGCCT                                 SEQ ID 10
4s. 5-GCCATCGTGGAAGCGA                                  SEQ ID 17
5a. 5-ACAGCCCGTCCCGCCGAT                                SEQ ID 8
```

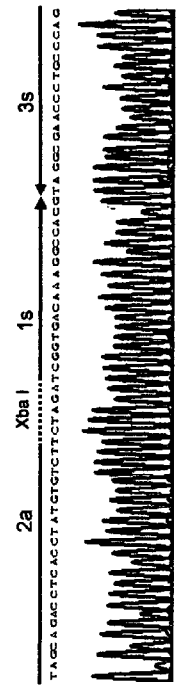

Figure 11C: Amplification products with different primer combinations

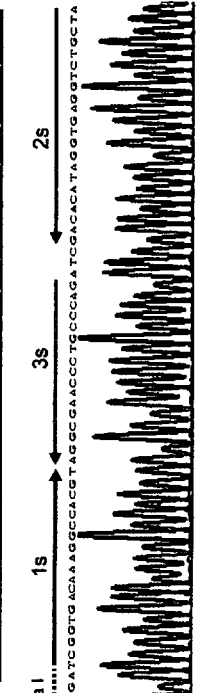

Figure 11D: Restriction digestion of amplification products

Figure 11E:
Sequence analysis of amplification products

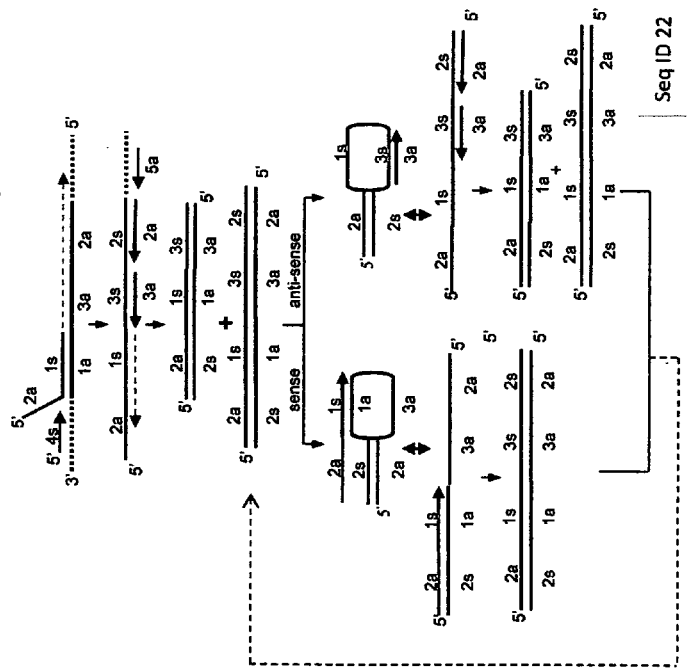

Figure 11A: Single Crossing Amplification

Legend for figure 11:

Fig.11A: Mechanism of single crossing amplification.

Fig.11B:Target sequence, primer locations and primer design. Note that an Xba I site (TCTAGA) was inserted into the cross primer between 1s and 2a.

Fig11C: Amplification products with different primer combinations. Lane 1: 1s, 2a and 3a; Lane 2: 1s, 2a, 3a, 4s and 5a; Lane 3: 1s, 3a, 4s and 5a; Lane 4: 1s, 2a, 4s and 5a; Lane 5: 2a, 3a, 4s and 5a; (-) indicates no target control for the corresponding reaction. The system works with minimum of 3 primers, and at least 1 of these to be cross primer. The 2 arrows point to the 2 smallest amplification products (1s/2a product and 1s/3a product, respectively), which are basic units as shown in figure 2a and the sequencing data (figure 2e). Note that in lane 3, the 1s/2a product is missing, and in lane 4, the 1s/3a product is missing. Lane 5 showed no product when the cross primer 1s is not present.

Fig.11D:The CPA amplification product digested by restriction enzyme Xba I. Lane1, CPA amplification product not digested; Lane 2, CPA amplification product digested by Xba I. High molecular weight products were reduced, indicating repetitive fragments, The digestion is not complete possibly due to the heterozygous secondary structures of the amplification products amplification products.

Fig.11E: Sequencing of CPA amplification products. The 2 bands indicated by arrows at figure 2c were excited, cloned and sequenced. The sequences correspond to the final products illustrated in figure 2a. The amplification products with higher molecular weight are tandem repeats of these basic units (data not shown).

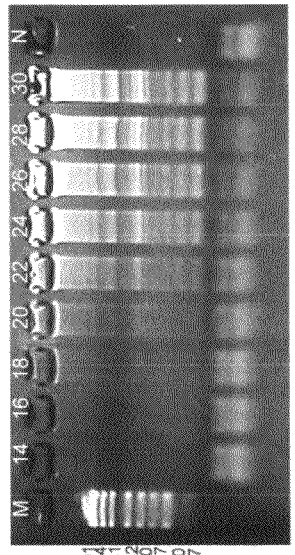

Figure 12B: Sensitivity test for TB-CPA
M. mark; 1. 10⁴copies/ml; 2. 10³copies/ml; 3. 10²copies/ml; 4. 10¹copies/ml; 5. 10⁰copies/ml; 6. Negative(60mins). 4 ul of the samples were used for each reaction.

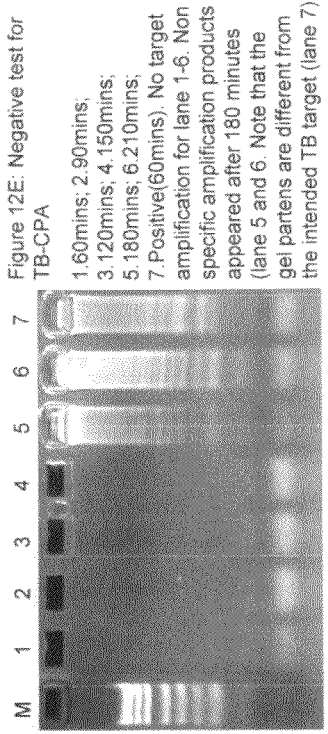

Figure 12D: Time course of single crossing amplification. Amplification reaction time indicated for each lane, from 14-30 minutes. M: marker; N: Negative control, 60 minutes. Target: cloned TB plasmid 10⁴ copies.

Figure 12E: Negative test for TB-CPA
1. 60mins; 2. 90mins; 3. 120mins; 4. 150mins; 5. 180mins; 6. 210mins; 7. Positive(60mins) No target amplification for lane 1-6. Non specific amplification products appeared after 180 minutes (lane 5 and 6. Note that the gel partens are different from the intended TB target (lane 7).

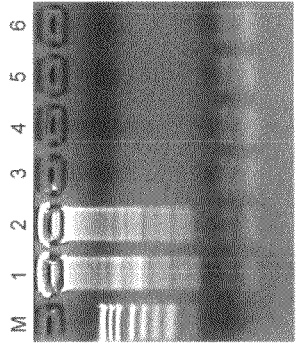

Figure 12: Performance of TB-CPA system

Figure 12A: Reaction temperature. CPA amplification reaction temperature ranging from 58 °C (data not shown) to 68 °C. 63 oC was selected for all of the experiments in this publication.

Figure 12C: Specificity of TB-CPA
1. Mycobacterium marinum; 2. Mycobacterium gordonae; 3. Mycobacterium Simiae; 4. Mycobacterium scrofulaceum; 5. Mycobacterium ranae; 6.Mycobacterium intracellulare 7. Mycobaterium Phlei ; 8. Mycobacterium smegmatis; 9. Mycobacterium vaccae; 10.Mycobacterium fortuitmn; 11. Mycobacterium chelonae subs. abscessus ;12. Mycobacterium chelonae subs.chelonae; 13. Mycobacterium tuberculosis; 14. Positive control (cloned plasmid) ; 15. Negative control

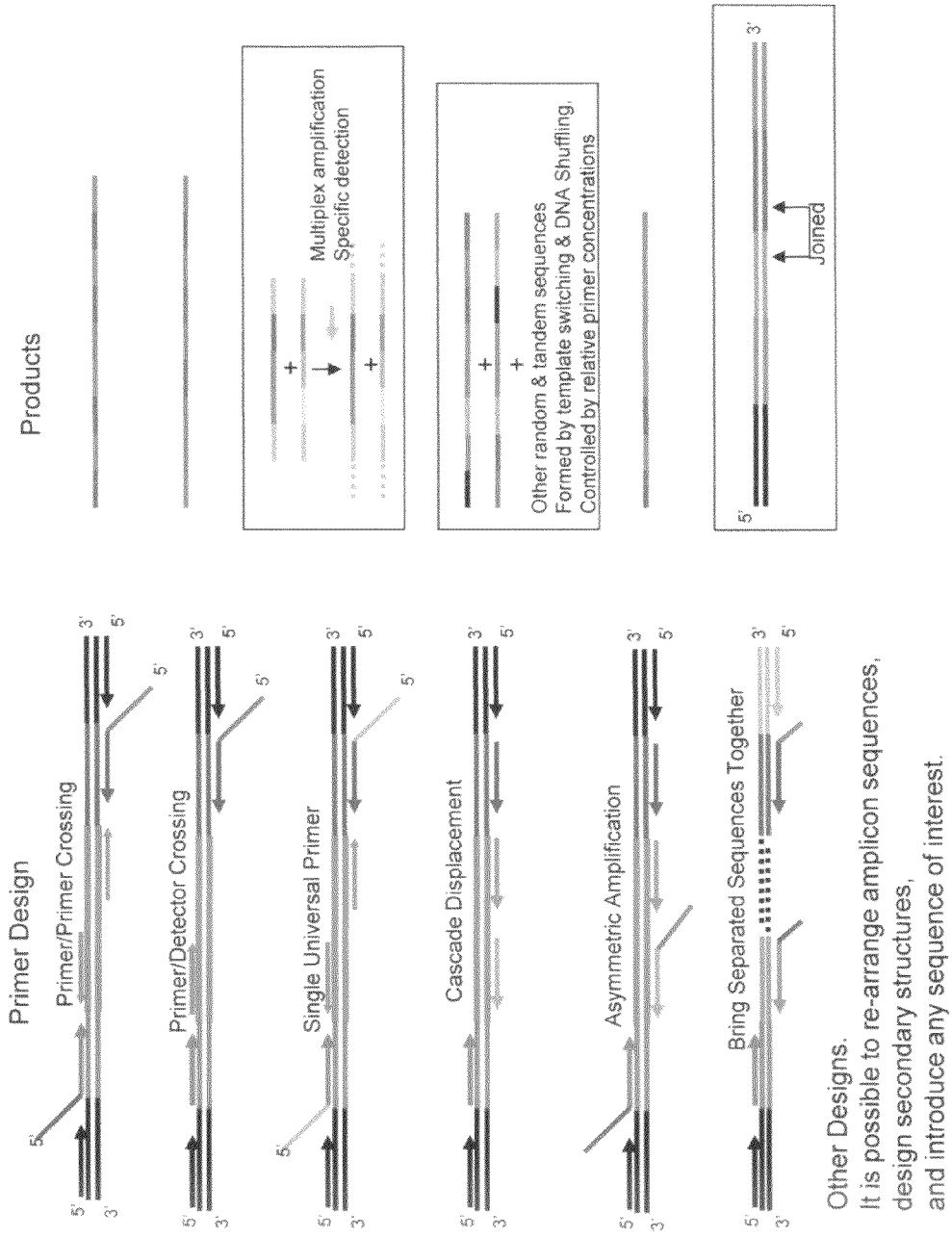

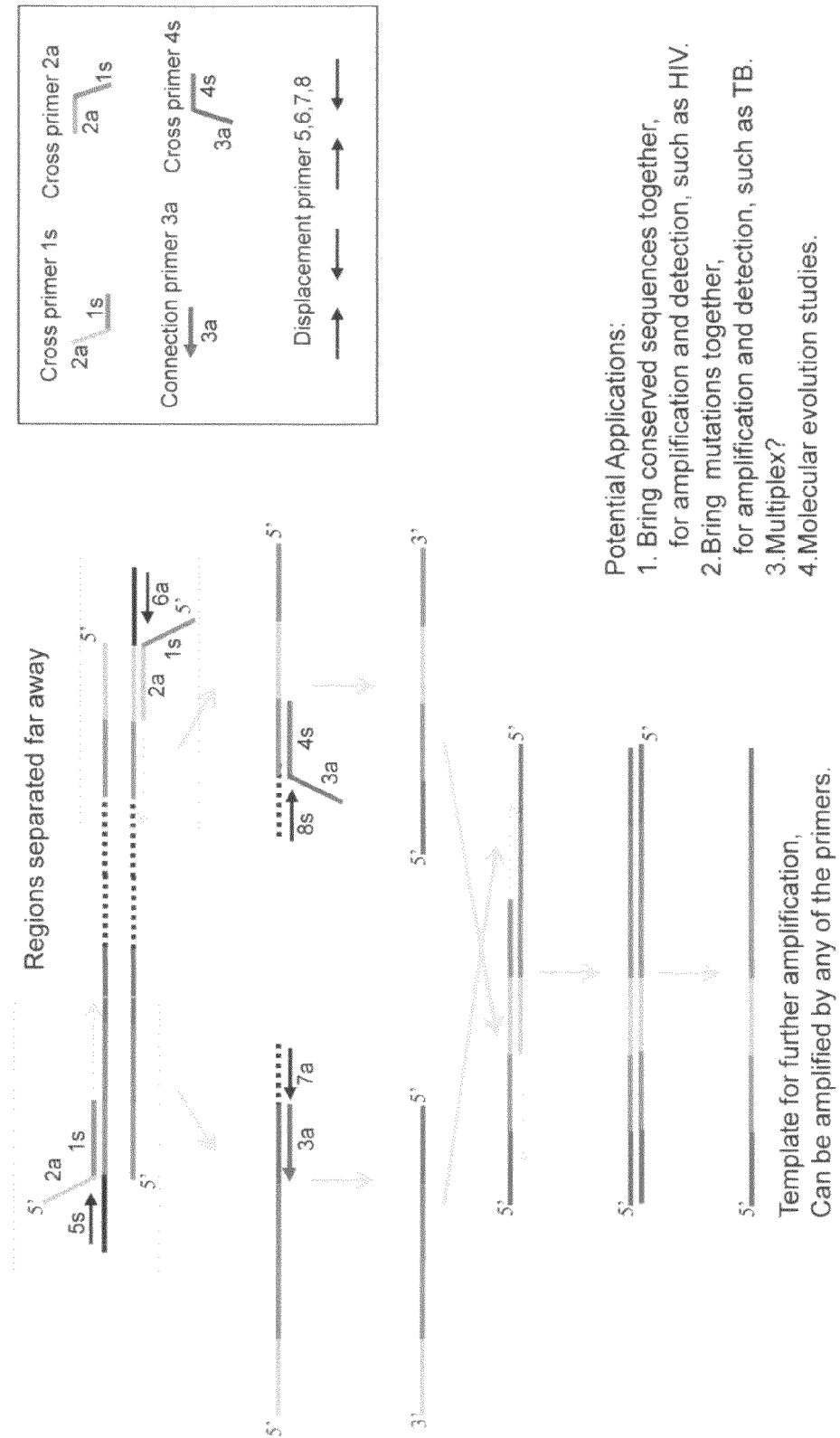

CROSS PRIMING AMPLIFICATION OF TARGET NUCLEIC ACIDS

This application claims benefit under 35 USC §119(e) of U.S. Provisional patent Application Ser. No. 61/398,798 filed Jul. 1, 2010.

FIELD OF THE INVENTION

The present invention relates to methods of cross primer amplification of target sequences and the amplification target sequence reagent kits and the applications.

BACKGROUND OF THE INVENTION

In the past 30 years, pathogenic microorganisms which are difficult to cultivate or can not be cultured have become the main source of contagious or infectious diseases. Prior art detection methods using markers such as number of proliferating bacterial colonies, colony purification separation, external morphology and physiological and biochemical identification as well as serological identification do not meet the fast, easy, high-specificity identification requirements of today because of their time-consuming, tedious steps and other shortcomings. Therefore, it is increasingly important to correctly identify these pathogenic microorganisms which are difficult to cultivate or cannot be cultured and to study these pathogenic bacteria nucleic acid structures and molecular characteristics at the molecular biology level thereby greatly enhancing the detection of such pathogenic bacteria. At present, highly sensitive, highly specific and rapid nucleic acid amplification technology can directly detect clinical specimens. However these techniques have been applied more widely in the infectious disease diagnoses and there is a trend to gradually replace traditional bacteria or virus cultivation.

Polymerase chain reaction (PCR) technology is the most widely used nucleic acid amplification technology currently employed. At present, the external nucleic acid amplification technology may be divided into two types. The first type is characterized by cycling temperatures in thermal insulation spots and includes PCR, ligase chain reaction (LCR), and transcription based amplification systems (TAS). The second type includes isothermal amplification systems such as the strand displacement amplification (SDA), nucleic acid sequence based amplification (NASBA), transcription mediated amplification (TMA), rolling circle amplification (RCA), loop-mediated isothermal amplification (LAMP), helicase dependent amplification (HDA). These methods all share the common characteristic that the amplification reactions are carried out under a uniform temperature so thereby simplifying the instrumentation required for the amplification reaction.

Most of various nucleic acid amplification technologies are coupled to various detection methodologies such as electrophoresis, fluorescence, mass spectrometry or direct sequencing so as to detect target sequences that are amplified. The detection technologies often involve complicated operations, are costly and usually require large-scale equipment that must be operated by skilled professionals. Furthermore, these techniques are often not suitable for broad application and use in many rural third world hospitals. The present invention combines isothermal nucleic acid amplification technology and nucleic acid testing strip rapid detection for simple, rapid, low cost detection of pathogens as well as other nucleic acid containing organisms.

As previously described there are several methods of nucleic acid amplification. PCR is accomplished by providing oligonucleotide primers at both sides of the target sequence so as to enzymatically synthesize several target sequence DNA fragments. Each cycle of PCR includes the DNA double strand separation, primer renaturation and an extension reaction catalyzed by the DNA polymerase which makes newly synthesized DNA fragments that may again become the templates for next cycle of amplification thereby giving rise to the exponential amplification of the target sequence DNA. At present, PCR technology has been applied widely in various aspects in the biotechnology such as detection of genetic diseases, cancer diagnoses and prognosis, identification of bacteria, viruses and fungal infection; and paternity.

LCR is amplification based on the connection capability of the Taq ligase, which is able to detect point mutations in a target gene sequence. LCR may identify the specific point mutation more readily than PCR. If there are any point mutations in the target sequence, the primer may not be connected with the target sequence precisely. The nucleotide special structure near the mutation has been varied so as that LCR may not be carried out and the amplification products may also not be generated. At present, the method is mainly used in the research and detection on the point mutation, such as the diagnoses of polymorphisms and products of single base hereditary diseases, research on specific identification of microorganisms and point mutations in the cancer genes.

RCA is divided into two types: linear amplification and exponential amplification. The former may only be applicable for annular nucleic acid amplification, whose products are a large number of DNA single strands of the repeated sequences complementary to the annular DNA. This technique may be suitable for specific signal detection on microarrays or in the solid-phase forms. In exponential amplification, the amplification products may also act as the templates thereby increasing amplification products exponentially. This technique may also be used for the non-annular DNA amplification. The specificity of RCA is very high, thus it can be used for mutation detection and SNP identification. Its use can be integrated with the fluorescent real-time detection, thereby enabling broad use of the technique.

TMA is amplification of RNA or DNA utilizing reverse transcriptase and T7 RNA polymerase under the isothermal conditions. In TMA reverse transcription of the target is accomplished by the action of the reverse transcriptase under the guidance a primer. The H activity of RNA reverse transcriptase degrades the RNA in the DNA-RNA hybrid chain thereby permitting the synthesis of double stranded DNA which can further be transcribed into thousands of RNA sequences under the action of T7 RNA polymerase. These RNAs may also act as the templates for next cycle. The whole TMA reaction is one autocatalytic process. The specificity of this method is high as is sensitivity. The reaction conditions are simple and the amplification efficiency is high. TMA does not require special amplification instruments and the whole reaction may be carried out in 1 test tube thereby reducing environmental pollution.

Amplification relying on the nucleic acid sequences, called self-sustained sequence replication (3SR), is used primarily for RNA detection. The reaction depends on the reverse transcriptase, T7 RNA polymerase, nuclease H as well as two special primers. The 3' end of the primer I, is complementary with the target sequence and its 5' end contains T7 RNA polymerase promoter for cDNA synthesis. The sequences of the primer II are complementary with the 5' end of the cDNA. During the reaction primer I is annealed to the RNA template to catalytically synthesize cDNA under the action of the reverse transcriptase. The RNA is then hydrolyzed by the nuclease H to form single-stranded DNA. Primer II is annealed to the 5' end of the cDNA and a second DNA strand is synthesized thereby forming a double-stranded DNA containing the T7 RNA polymerase promoter. Reverse transcriptase is used to transcribe a new RNA strand that is identical to the sample RNA sequence. Each new RNA strand may also act as the template to synthesize cDNA. The process may be repeated to form more RNAs and cDNAs. The operation is simple; no special instrument is required; no temperature cycling is required. Amplification may not be effective if the double stranded DNA has no any promoter sequence so if the reaction specificity is increased greatly. This technology is suitable for detecting and quantitatively analyzing specific RNA and also applicable for amplifying double stranded DNA. Therefore, it may be applied widely in the clinic.

SDA relies on the use of restriction endonuclease and DNA polymerase. SDA requires single-strand DNA template preparation in which DNA fragment of interest is generated in which the two ends of the fragment include enzyme sites for SDA cycling. A primer containing the restriction endonuclease identification sites is combined with the single-stranded target molecules to form double-stranded DNA with semi-phosphorylation sulfation sites by the action of DNA polymerase which has no excision enzyme activity. The unprotected primer chain is cut by the restriction endonuclease; whereas, the modified target fragments remain intact and the DNA polymerase starts the extension at the notch location and replaces the downstream sequences so as to generate another DNA single strand whose notch may be opened by the restriction endonuclease. Such opening notches, polymerization and replacement procedures are recycled repeatedly thereby generating a large number of complementary strands of target molecules. SDA has the high sensitivity and can rapidly amplify single-stranded molecules; however, its application range is restricted because of the complexity of the target sequence preparation and detection method limitations.

LAMP is mainly made up of the Bst large-fragment DNA Polymerase and two pairs of special internal primers (FIP being made up of F1C and F2; BIP being made up of BIC and B2) and one pair of the external primer (F3 and B3). The F2 sequence of the FIP primer is coupled with the complementary sequence in the target DNA and the loop strand displacement reaction may be started. The F3 primer is complementary with the F3C area in the template to bring about and synthesize the double strands of the template DNA so as to crowd out the DNA single strand introduced by FIP. In the meantime, the BIP primer is combined with the crowded out single strand hybridization so as to open the formed annular structure. Then the B3 primer is coupled with the base at the BIP outer side to form the new complementary strand under the action of the polymerase. There are the complementary sequences in the both ends of the displaced single-stranded DNA so as that the self base coupling may occur to form the dumbbell DNA structure, which may act as the starting structure for LAMP reaction to recycle and extend and a large number of DNA sequences are generated repeatedly and alternatively to form the amplification products, which are cauli-stem-loop structure DNA with many loops and in the cauliflower shape. LAMP is highly specific and highly sensitive. Detection of pathogenic microorganisms using LAMP can be both qualitative and quantitative as there is a linear relation between the quantity of magnesium pyrophosphate precipitation generation and the quantity of DNA generated. LAMP has a simple experimental setup and the experiments are isothermal, thus only an ordinary water bath or other devices which can act as the stable heat source may be required. This method may have applicability for scientific research work as well as a routine detection tool.

TAS is primarily used for the amplification RNA. It utilizes reverse transcriptase, T7 RNA polymerase and nuclease H as well as two special primers. The 3' end of the primer I is complementary with RNA for amplification and its 5' end contains the promoter information of T7 RNA polymerase. The reverse transcriptase synthesizes cDNA by using primer I as the starting point. Primer II is complementary with the 3' end of this cDNA and is used to synthesize the second strand of the cDNA. T7 RNA polymerase transcribes RNA which is the same as the RNA for amplification by taking the double stranded DNA as the template, which may be the template for the next round reaction. The TAS is with high amplification efficiency and its specificity is high; whereas, its cycling processes are complicated and the reverse transcriptase and T7-RNA polymerase may be added repeatedly; therefore, its further study will be carried out.

HDA is a method that simulates natural DNA duplication, as it uses unwindases to separate DNA strands. HDA may be carried out under the same temperature so as to optimize synthesis thereby reducing cost and power consumption that a thermal cycler would require. The present invention provides a method of isothermal amplification and nucleic acid detection in which one kind of strand displacement DNA polymerase (preferably Bst DNA polymerase) can be maintained for dozens of minutes at some certain constant temperature (about 62° C.), to carry out nucleic acid amplification reactions. Therefore, the methods of the present invention provide rapid nucleic acid amplification may be carried out quickly and effectively and in which only one simple thermostatic apparatus is required to carry out all amplification processes so as to greatly decrease the complexity of the reaction (No thermocycler required). The methods of the present invention also couple nucleic acid detection testing strip detection with cross priming amplification so as to develop one new rapid nucleic acid detection method which enable amplification and detection processes to be accomplished easily and simply. Template thermal denaturation, long-time temperature cycling, tedious electrophoresis and other processes are no longer required. The methods of the present invention are specific, simple and quick and may be applied broadly, with applications including diagnoses on the molecules directly related to human genetic diseases, detection of pathogenic microorganisms, estimation on the tumor or cancer diagnoses and prognosis and microorganism typing. Some isothermal amplification methods require initial denaturation of target DNA (Genomic DNA) at higher temperature before the isothermal reaction. CPA does not require initial thermal denaturation as it is truly an isothermal method.

SUMMARY OF THE INVENTION

The present invention relates to novel technology and methods for the amplification of nucleic acid sequences. More particularly, the present invention relates to methods of amplification of nucleic acids by utilizing cross priming isothermal amplification. Further the present invention relates to methods of marking the amplification target sequence during the amplification reaction and rapid detection of the target sequence. The present invention also relates to the use of the methods in reagent kits for the rapid detection of nucleic acid sequences of pathogenic microorganisms such as bacteria, and viruses. The amplification and detection methods of the present invention can also be utilized in the detection and diagnosis related to human genetic diseases.

Cross Priming Amplification (CPA) uses multiple cross-linked primers, typically from 3 to 8 primers which can be paired, in which DNA target sequence is amplified at one constant temperature, using a simple heating device such as a water bath or a dry incubator. The number of primer/detector can be variable, according to the purpose and optimization. The cross sequence can be designed for primer/primer cross, or primer/detector cross, or other formats to satisfy different applications.

The detection of amplified products may be performed on a lateral flow strip which may be housed in a sealed plastic device such as that described in US Patent Publication No. 2009/0181388A1, which prevents the leakage of amplicons. During the reaction, the amplification products are hybridized and labeled simultaneously, thereby making the labeled amplified target ready for detection in a cross contamination-proof lateral flow DNA strip device which provides a visual display read-out of the assay results.

In general CPA involves the generation of cross priming sites, cross priming amplification and generation of detectable products. Forward cross primer sense (PFs) and reverse cross primer anti-sense (PRa) primers are designed with 5' sequences identical to each other's priming sequence. Displacement primers are designed that are located upstream of the cross primers. In preferred embodiments the concentration of displacement primers are lower than that of the cross primers. DNA polymerase (in preferred embodiments Bst) extends the cross primer, and extend the displace primer. The extension of displacement primer displaces the cross primer extension strand, with a defined 5' end. A similar extension/displacement mechanism on this new strand adds another priming site, PFa on the other strand and also creates the other defined end.

The displaced strand contains newly introduced priming sites on both ends, and serves as template with priming sites for both cross primers on its 3' end. A new priming site is introduced after each round of extension/displacement, resulting in multiple primer binding sites which accelerate the amplification process.

The intermediate and end products are mixed in that they have different lengths, and may have many forms of secondary structures (single stranded, double stranded or partial double stranded). Detector probes or primers are used to probe for the target sequence. In a preferred embodiment one primer is extendable while the other is not extendable and these primers hybridize to the amplification products. Products that are linked to both detectors are detectable, and in a preferred embodiment the detection mechanism utilizes a lateral flow strip detection platform.

CPA utilizes the strand displacement function of DNA polymerase (such as Bst, Klenow, Vent exo-DNA polymerase) to denature double stranded DNA. The use of such polymerase is shared by most isothermal amplification methods, including SDA, LAMP, CPA, RCA (Rolling Circle Amplification), HDA (Helicase Dependent Amplification).

SDA, LAMP and CPA all utilize a 5' tail for some primers, but whereas the purpose of 5' tail in SDA is to introduce a nicking enzyme recognition site to the target and the purpose of 5' tail in LAMP is to introduce a sequence to form a loop in the target, the primary purpose of 5' tail in CPA is to introduce additional priming sites at both ends of the target.

In SDA, the DNA extension mainly relies on nicking to create a free 3' end, annealed to the template strand for the synthesis of new DNA. In LAMP, the DNA extension mainly relies on the forming of self folding loop, to anneal the free 3' end of the loop to the template strand for the synthesis of new DNA. In CPA, the DNA extension mainly relies on the annealing of multiple primers to multiple priming sites of both strands to drive the synthesis of new DNA.

The methods of the present invention includes methods for amplifying a target nucleic acid sequence comprising:

a) designing at least a first cross amplification primer and a second cross amplification primer wherein the cross amplification primers comprise a hybridization sequence and an interchanging sequence and at least a first displacement primer and a second displacement primer wherein the first displacement primer is located 5' to the first cross amplification primer and wherein first displacement primer is located 5' to the first cross amplification primer;

b) generating cross priming sites by introducing the cross amplification primers and the displacement primers to a target sequence in the presence of a DNA polymerase under isothermal conditions such that cross priming hybridization sites are introduced into the ends of the target nucleic acid sequence thereby producing a target nucleic acid sequence containing cross amplification primer sites; and c) amplification of the target nucleic acid sequence containing cross amplification primer sites through repeated hybridizations and extensions of the cross hybridization primers.

The methods of the present invention include methods for detecting the presence of a target nucleic acid sequence comprising:

a) designing at least a first cross amplification primer and a second cross amplification primer wherein the cross amplification primers comprise a hybridization sequence and an interchanging sequence and at least a first displacement primer and a second displacement primer wherein the first displacement primer is located 5' to the first cross amplification primer and wherein first displacement primer is located 5' to the first cross amplification primer;

b) generating cross priming sites by introducing the cross amplification primers and the displacement primers to a target sequence in the presence of a DNA polymerase under isothermal conditions such that cross priming hybridization sites are introduced into the ends of the target nucleic acid sequence thereby producing a target nucleic acid sequence containing cross amplification primer sites; and c) amplification of the target nucleic acid sequence containing cross amplification primer sites through repeated hybridizations and extensions of the cross hybridization primers;

d) introducing a first detection primer labeled with a first marker and a second detection primer labeled with a second marker to the amplified target nucleic acid sequence containing cross amplification primer sites wherein the introduction of the first and second detection primers produces double stranded nucleic acid molecules containing both markers; and e) detecting the double stranded nucleic acid molecules containing both markers.

The present invention also provides for kits for detecting pathogenic microorganisms, environmental microorganisms, microorganism typing, infectious disease pathogens for detecting human, animals or plants, infectious disease pathogens for detecting foods or biological weapons, the detection human genetic diseases or health risk genes comprising cross amplification primers, displacement primers, detection primers and DNA polymerase as well as nucleic acid strip detection which may be placed within a contamination-free device.

BRIEF DESCRIPTION OF THE DRAWINGS

FIG. 2—A schematic diagram of the basic primer design of a preferred embodiment of the cross primer amplification method of the present invention, including the cross amplification primer and detection primer site and sequence arrangement.

FIG. 3B—A schematic diagram of a preferred embodiment of the amplification phase of the cross priming amplification method using a linear structure form which generates multiple priming sites.

FIG. 3C—A schematic diagram of a preferred embodiment of the amplification phase of the cross priming amplification method using a secondary structure forms, multiple primer binding and self fold and extension multiple priming sites.

FIG. 8B—A target sequence, primer location and primer design for *Mycobacterium tuberculosis* in which an XbaI site is inserted into cross primer between 1s and 2a.

FIG. 8C—Amplification products with different primer combinations. Lane 1: 1s, 2a and 3a; Lane 2: 1s, 2a, 3a, 4s and 5a; Lane 3: 1s, 3a, 4s and 5a; Lane 4: 1s, 2a, 4s and 5a; Lane 5: 2a, 3a, 4s and 5a; (-) indicates no target control for the corresponding reaction. The system works with minimum of 3 primers, and at least 1 of these to be cross primer. The 2 arrows point to the 2 smallest amplification products (1s/2a product and 1s/3a product, respectively), which are basic units as shown in FIG. 2a and the sequencing data (FIG. 2e). Note that in lane 3, the 1s/2a product is missing, and in lane 4, the 1s/3a product is missing. Lane 5 showed no product when the cross primer 1s is not present.

FIG. 8D—The CPA amplification product digested by restriction enzyme Xba I. Lane 1, CPA amplification product not digested; Lane 2, CPA amplification product digested by Xba I. High molecular weight products were reduced, indicating repetitive fragments, The digestion is not complete possibly due to the heterozygous secondary structures of the amplification products amplification products.

FIG. 9B—Gel image of heterozygous amplification products

FIG. 10A: Schematic of mechanism of double primer crossing amplification.

FIG. 10B: Schematic of Cross Priming Amplification (double crossing)

FIG. 10C: Gel image of heterozygous amplification products

FIG. 10D: Sequencing of an amplification product

FIG. 11A: Schematic of Single Crossing Amplification

FIG. 11B: Target sequence, primer locations and primer design

FIG. 11C: Gel of Amplification products with different primer combinations

FIG. 11D: Gel of restriction digestion of amplification products

FIG. 11E: Sequence analysis of amplification products Legend for FIG. 11:

FIG. 11A: Mechanism of single crossing amplification.

FIG. 11B: Target sequence, primer locations and primer design. Note that an Xba I site (TCTAGA) was inserted into the cross primer between 1s and 2a.

FIG. 11C Amplification products with different primer combinations. Lane 1: 1s, 2a and 3a; Lane 2: 1s, 2a, 3a, 4s and 5a; Lane 3: 1s, 3a, 4s and 5a; Lane 4: 1s, 2a, 4s and 5a; Lane 5: 2a, 3a, 4s and 5a; (-) indicates no target control for the corresponding reaction. The system works with minimum of 3 primers, and at least 1 of these to be cross primer. The 2 arrows point to the 2 smallest amplification products (1s/2a product and 1s/3a product, respectively), which are basic units as shown in FIG. 2a and the sequencing data (FIG. 2e). Note that in lane 3, the 1s/2a product is missing, and in lane 4, the 1s/3a product is missing. Lane 5 showed no product when the cross primer 1s is not present.

FIG. 11D The CPA amplification product digested by restriction enzyme Xba I. Lane 1, CPA amplification product not digested; Lane 2, CPA amplification product digested by Xba I. High molecular weight products were reduced, indicating repetitive fragments, The digestion is not complete possibly due to the heterozygous secondary structures of the amplification products amplification products.

FIG. 11E: Sequencing of CPA amplification products. The 2 bands indicated by arrows at FIG. 2c were excited, cloned and sequenced. The sequences correspond to the final products illustrated in FIG. 2a. The amplification products with higher molecular weight are tandem repeats of these basic units (data not shown).

FIG. 12A: Gel of different reaction temperatures.
FIG. 12B: Gel of Sensitivity test for TB-CPA.
FIG. 12C: Gel of Specificity of TB-CPA.
FIG. 12D: Gel of time course of single crossing amplification.
FIG. 12E: Gel of negative test for TB-CPA
FIG. 13: Schematic of Assay Design Flexibility
FIG. 14: Theoretical Schematic of assembling of separated sequences

DETAILED DESCRIPTION OF THE INVENTION

Figure 1:
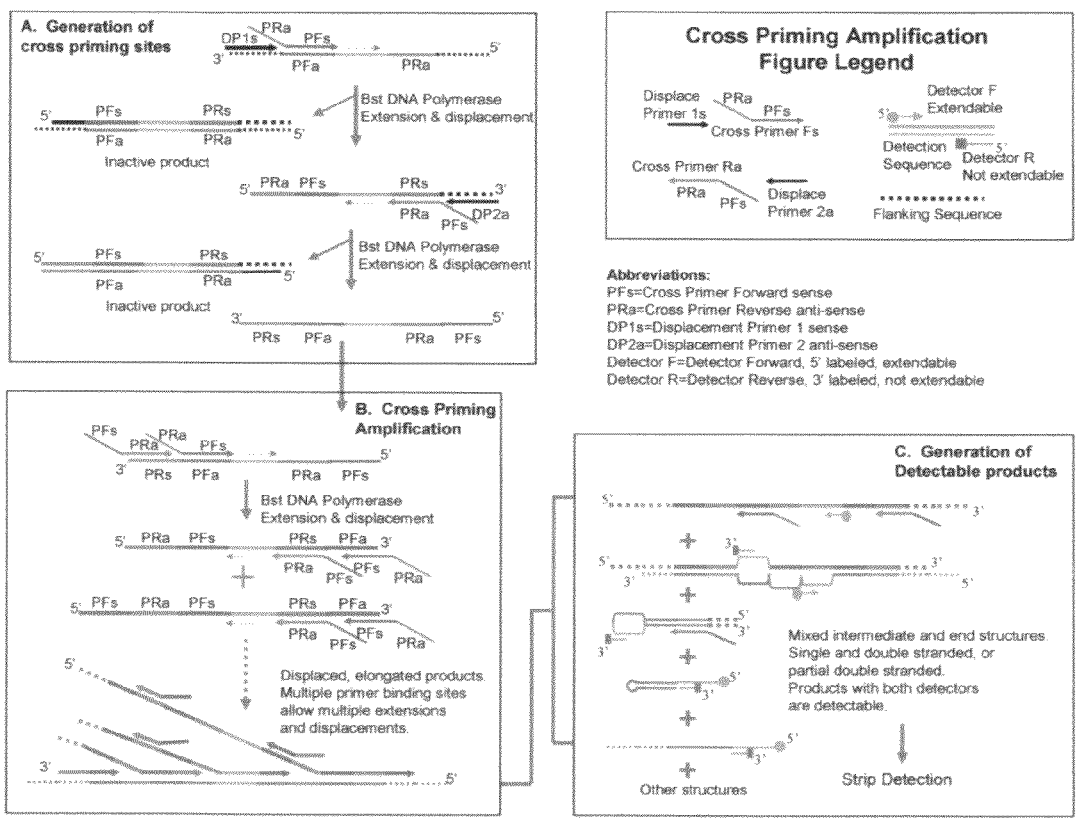
FIG. 1—A schematic diagram of the basic concept of cross primer amplification.

The present invention relates to novel technology and methods for the amplification of nucleic acid sequences. More particularly, the present invention relates to methods of amplification of nucleic acids by utilizing cross priming isothermal amplification. Methods of the present invention named cross priming amplification utilize at least 6 types (3 pairs) of specific primers which are designed according to 6 areas of the target nucleic acid. The amplification methods may be carried out under constant temperature (isothermal) by using chain replacement DNA polymerases such as, but not limited to Bst DNA polymerase. The processes of the present invention therefore may not require template thermal denaturation or temperature cycling.

A preferred embodiment of the cross priming amplification methods of the present invention include the following procedures:

Primer design—Primer design may include one pair of cross amplification primers, one pair of displacement primers and one pair of detection primers.

Starting phase—Cross priming hybridization sites may be introduced into each end of the amplification target sequence. A fixed end may also be generated so as to prepare the template for rapid amplification.

Amplification phase—The amplification may be carried out in either the linear structure or secondary structure mode. Several primer hybridization sites may be generated and are carried out through the repeated hybridizations and extensions of the primers and the self-hybridization folding and extensions of the amplification products so that several amplification reactions may be carried out simultaneously in the same template.

Detection of the products generated—Detection primers may be used to synthesize dually-marked DNA double stranded molecules for detection by taking the amplification products containing a large number of detection sequences which are generated during the amplification phase as the template. The amplification products may then be detected by using the nucleic acid detection testing strips.

Primer design may include one pair of cross amplification primers, one pair of displacement primers and one pair of detection primers. In preferred embodiments of the methods of the present invention one pair of cross amplification primers (cross amplification primer F and cross amplification primer R) are synthesized. Cross amplification primer F and cross amplification primer R may be comprised of three segments:

1) Hybridization sequences—these are base sequences which hybridize with the template with high specificity for the amplification extension.

2) Connectors—nucleotides used to connect two different sequences in the primer, generally 1-3 mononucleotides.

3) Interchanging sequence—the hybridization sequence of the cross amplification primer F, which may also be the 5' end sequence of cross amplification primer R; in like fashion, the hybridization sequence of the cross amplification primer R may act as the 5' end sequence of cross amplification primer F. (FIG. 2).

One pair of displacement primers (displacement primer F and the displacement primer R) may be synthesized in which displacement primer F is the forward outer primer that is complementary with the antisense strand of the target gene and displacement primer R is the 5' outer primer that is complementary with the sense strand of the target gene. The displacement primer F and the displacement primer R are primarily used for lengthening the strands of the displacement cross amplification primer during the starting phase in the isothermal amplification reaction. (FIG. 2).

Figure 4:
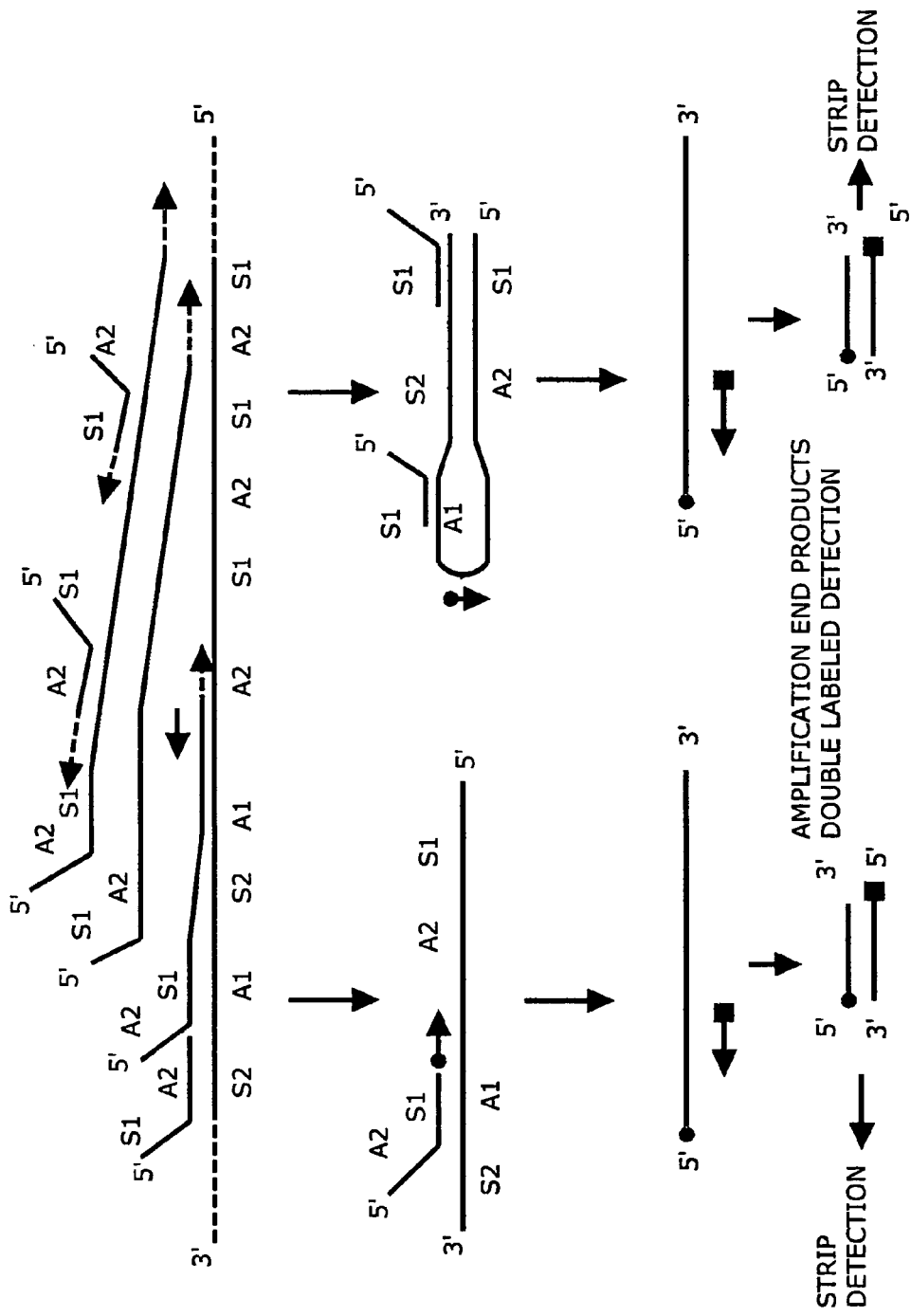
FIG. 4—A schematic diagram of the generation amplified products and the detection of amplified products which are double labeled.
Figure 5:
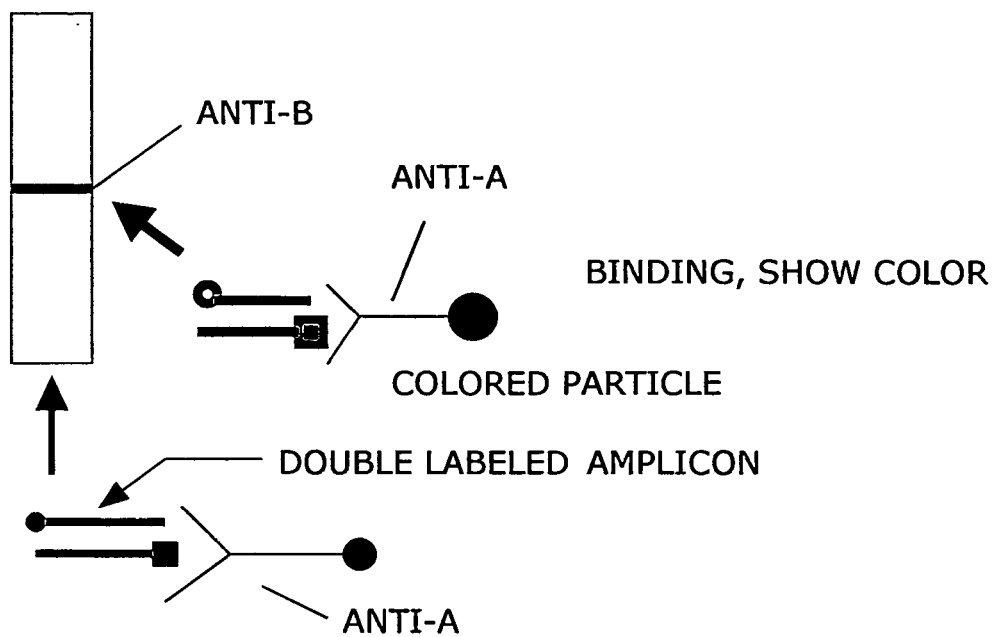
FIG. 5—A schematic diagram outlining one method of detecting the amplification products by using the nucleic acid detection testing strips FIG. 6—The results of detecting the amplification products of *Chlamydia trachomatis* by testing strips.
Figure 5:
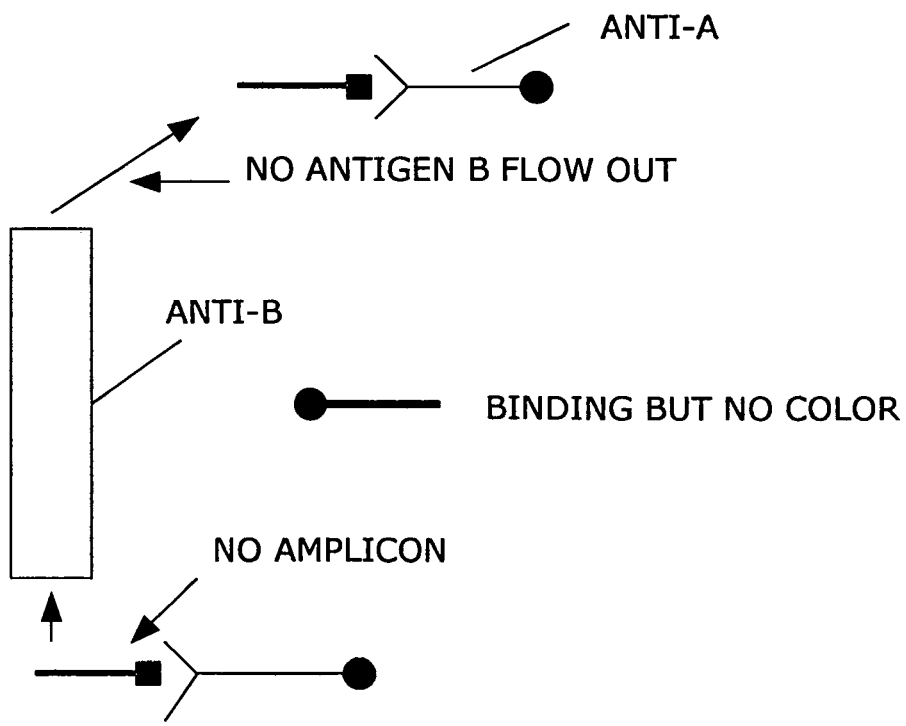

One pair of detection primers (the detection primer F and the detection primer R) may be synthesized in which the detection primer F is the backward inner primer that is complementary with the sense strand of the target gene and the detection primer R is the forward inner primer that is complementary with the antisense strand of the target gene. The pair of primers are marked by at least one different marker (preferably a hapten antigen), respectively, thus when amplifying the target sequence the products of that amplification can be detected by the presence of the dual antigen (FIGS. 2, 4, 5).

During the starting phase cross priming hybridization sites may be introduced into the each end of the amplification target sequence and fixed ends may be generated so as to prepare desired template for rapid amplification. CPA utilizes the strand displacement function of DNA polymerase (such as Bst, Klenow, Vent exo-DNA polymerase) to denature double stranded DNA. To permit hybridization between the forward amplification primer F and the nucleic acid target molecules the primers are designed such that there are hybridization identification sequences of the backward primer R in the 5' end of the forward primer F. The double stranded nucleic acid may be synthesized by the DNA polymerase extension forward amplification primer F with displacement function. To cause the hybridization between the forward displacement primer F and the nucleic acid target molecules. To use the DNA polymerase extension displacement primer F with the displacement function and the extension strand of the displacement forward amplification primer F to generate the fixed forward strand 5' end.

The hybridization may be carried out between the displacement amplification primer extension strand as the template and the backward amplification primer R, at whose 5' end there is the hybridization identification sequence of the forward primer F. The double stranded nucleic acid may be synthesized by the DNA polymerase extension backward amplification primer R with displacement function. The hybridization is carried out by using the backward displacement primer R and nucleic acid target molecules.

Figure 3A:
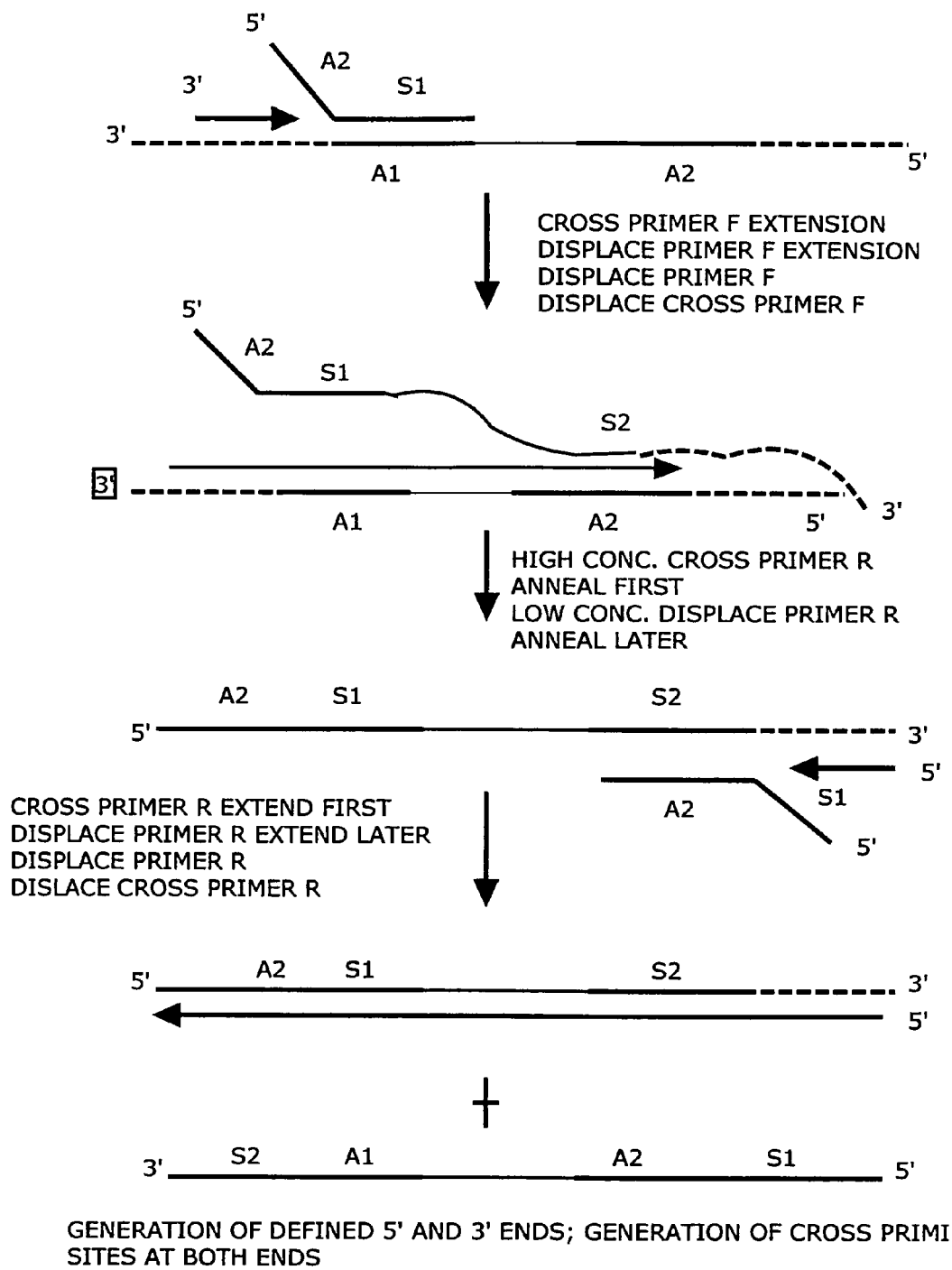
FIG. 3A—A schematic diagram of a preferred embodiment of the initiation phase of the cross priming amplification method including the generation of cross priming sites and defined ends.
Figure 3A:
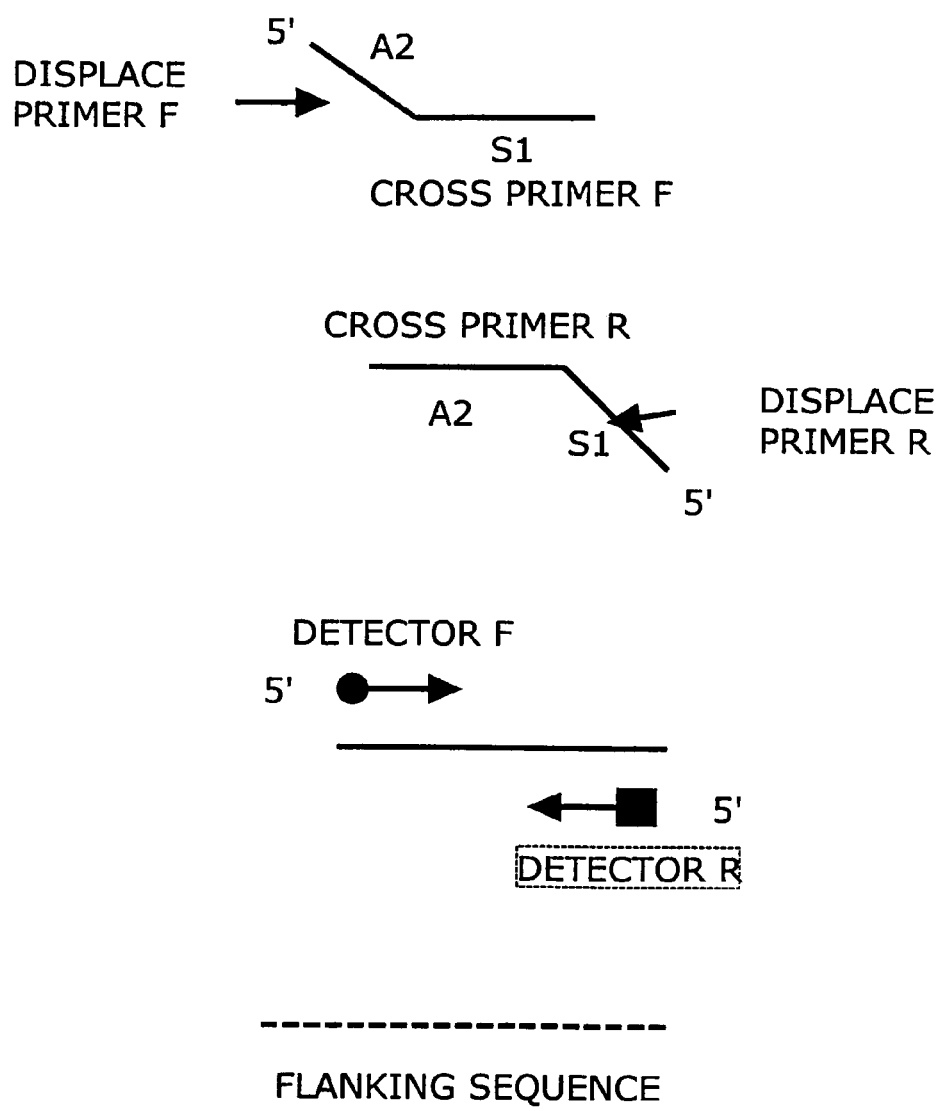

To use the DNA polymerase extension displacement primer R with the displacement function and the extension strand of the backward amplification primer R to generate the fixed backward strand 5' ends. Both ends of the generated backward amplification primer R extension strand have been fixed at this time; the hybridization sequences of the amplification primers F and R are introduced into the 3' end and the 5' end, respectively, so as to act as the templates for rapid amplification. (FIG. 3A)

Figure 3B:
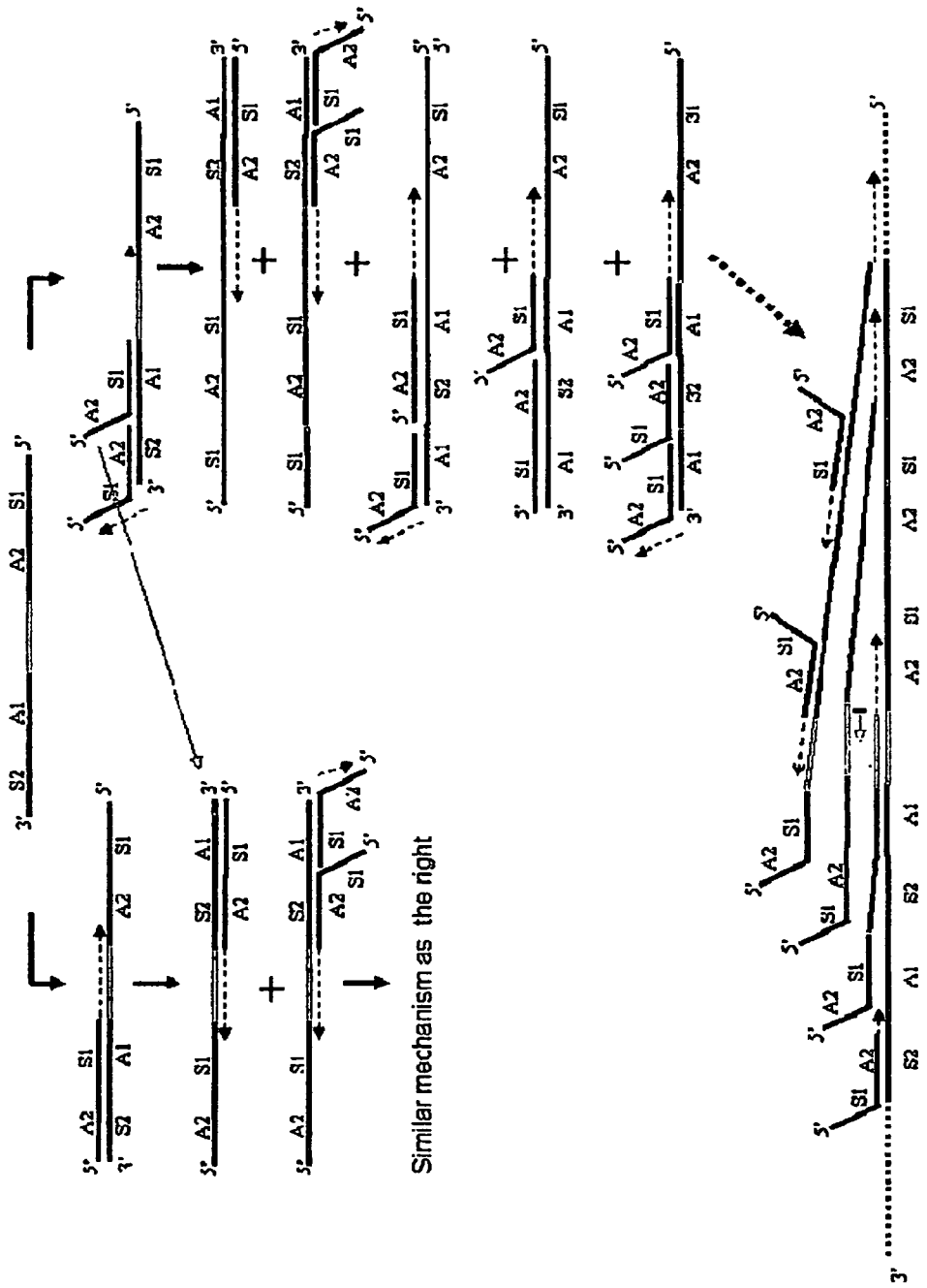
Figure 3:
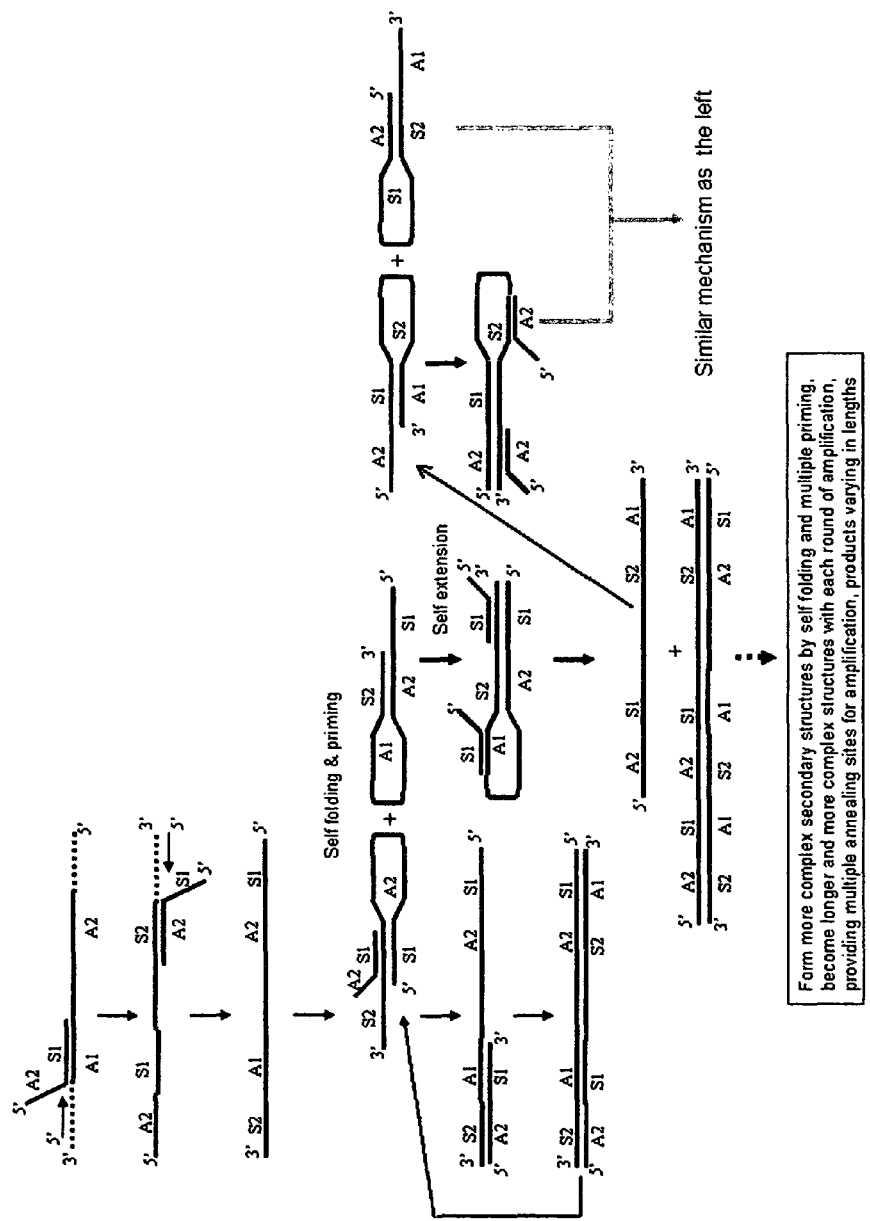

Amplification may be carried out in either a linear structure (FIG. 3B) and/or secondary structure mode (FIG. 3C). Multiple primer hybridization sites are generated and are amplified throughout the repeated hybridizations and extensions of the primers and the self-hybridization folding and extensions of the amplification products so as that several amplification reactions may be carried out simultaneously in the same template. Primer extensions at the ends displace the extension strands, which may be again be used as the template to participate in the next round of amplification so as to greatly enhance the amplification speed.

In the linear structure mode, one new primer hybridization sequence may be introduced into the amplification primer for every extension and the amplification products may be lengthened along with every round of amplification. Primer hybridization opportunities are increased because of the increased synthesizing speed of short strand products such that the most of the final products may be the short strand products. In other words, the products by using the cross priming amplification method may be the mixture of amplification products of different lengths, in which the long stranded amplification products may provide the multiple primer hybridization sites for further amplification thereby enhancing the amplification speed and the short stranded amplification products may be the main objects for the final detection. (FIG. 3A).

In the secondary structure mode, the amplification products may form various complicated secondary structures through self-folding due to the presence of repeated complementary sequences in the long strand amplification products. These amplification products can be longer and the structures more complicated through self extension and because single strands may provide primer hybridization for synthesis of new amplification products. The linear structure and the secondary structure may be interchanged. The single-stranded linear structure and secondary structure molecules may be interconnected through hybridization so as to form huge DNA hybridization complexes. Therefore, the products in the cross priming amplification method are very complicated as determined by gel electrophoresis. Different length DNAs may be seen and huge DNA hybridization complexes are located in the sampling wells of gel electrophoresis as they have almost no mobility.

After amplification the products can be detected in various fashions. In a preferred embodiment detection primers may synthesized each containing one or more different markers. The resulting dually marked DNA double stranded molecules can be detected by taking the amplification products containing a large number of detection sequences which are generated during the amplification phase. Most of such dually marked DNA double stranded molecules are relatively short amplification final products; whereas, the relatively large amplification products or huge hybridization complexes contains the hybridization sites of the detection primers, which may obtain the dually marking through the detection primer hybridization; thus they may be detected. (FIG. 4).

The amplification products of the dually marked target sequences may be detected through agarose gel electrophoresis or nucleic acid detection testing strips. One embodiment of the detection principal of the nucleic acid testing strip is shown in FIG. 5.

The schematic for a single crossing assay for CPA is shown in FIG. 11A. In the single crossing assay, the primer set is designed to increase the abundance of small amplicons while still providing the features necessary for overall amplification of the target sequence in the template. The primary function of cross primer 1s is identical to that in the double crossing assay: to allow strand displacement and to incorporate a second defined priming site in the 5' end of the resulting product. Primers for the opposite strand each consist of a single sequence complementary to the template, and are chosen so that they bind in tandem on the template, in essence providing a region of nicked double stranded DNA that can be extended by a strand displacing DNA polymerase. The displaced single stranded product from both strands are complementary at their 5' and 3' ends by virtue of the introduction of the 2a sequence at the 5' end of the top strand and the 2s sequence at the 3' end. These single stranded DNAs are able to form hairpin-like structures stabilized by the 19 base pair double helix formed between 2a and 2c, and can act as templates for further extension reactions (FIG. 11A).

FIG. 11B shows a set of five primers to the IS6110 region of *Mycobacterium tuberculosis* genomic DNA for a single crossing amplification reaction. Amplification reactions were carrier out in the presence of template DNA using various combinations of the 5 primers (FIG. 11C). The two arrows point to the 1s/2a amplification product (top) and the 1s/3s amplification product (bottom), which are the basic units shown in FIG. 10A. Both products are obtained using solely the 1s, 2a and 3a primers (lane 1), but the yield is enhanced when primers 4s and 5a are also included in the reaction (lane 2). When primer 2a is omitted from the mix (lane 4). If the cross primer 1s is not present in the reaction, there are no products produced from the mixture of four primers (lane 5). These result demonstrate that the system works with a minimum of three primers as long as one of these primers is a cross primer. (e.g. primer 1s).

The reaction scheme does not predict the formation of the higher molecular weight amplicons observed in a single crossing reaction products shown in FIG. 11C. To determine whether these products represent tandem copies of the basic amplicons, the reaction products were digested with Xba I, which is introduced in the design of the 1s primer. The higher molecular weight products of the single crossing amplification reaction are reduced in size upon digestion with Xba I (FIG. 11D) as are the 1s/3a and 1s/2a basic products. The incomplete digestion of the higher molecular weight fragments may be the result of their ability to form a variety of secondary structures which might interfere with restriction enzyme cleavage at some Xba I sites.

The two bands corresponding to the smallest amplification products (FIG. 11C) were excised from the gel, ligated into a TA vector and sequenced. The sequences obtained correspond to the predicted 1s/3a and 1s/2a final products (FIG. 11E). The amplification products with higher molecular weight were cloned and sequenced and are tandem repeats of the 1s/3a and 1s/2a basic units.

CPA offers a great deal of flexibility through different primer design strategies and by controlling the ratio of the various primers (FIG. 13). Of particular interest are the strategies for asymmetric amplification, multiplex amplification coupled to specific detection and detection of separated target areas by encouraging template switching and DNA shuffling in a controlled fashion. This last application of interest in designing amplification protocols to detect pathogens that undergo rapid mutation and have only a small conserved sequence area widely dispersed in their genomes. CPA combined with careful primer design can result in the production of initial extension products that combine the dispersed conserved regions in a tandem fashion thus producing a template for further amplification and detection (FIG. 14).

CPA can be used for single universal primer detection of multiple targets. CPA may be designed to detect different pathogens simultaneously with a universal tail. Two sets of specific primers with a universal tail are used to amplify the specific pathogen with low concentration in the initial stage. The amplicons with the universal sequence at both 5' and 3' ends are further amplified by a single universal primer, which is at a higher concentration. Specific amplicons from different targets are (if present in the sample) may "fuse" to for a heterogenous template and be amplified and distinguished by a specific detector probe.

The optimal temperature for an isothermal amplification assay must balance binding of the primer to the template strand with elongation activity of DNA polymerase. Single crossing amplification reactions were carried out at different temperatures using M. tuberculosis DNA as with the appropriate primers. Roughly equivalent levels of amplicons were observed to form in a template-dependent manner at temperatures ranging from 63° C. to 68° C., but failed to form 70° C. (FIG. 12A). Temperatures below 63° C. gave little to no product. A reaction temperature 63° C. was selected as the standard temperature for the rest of the CPA assays conducted.

The minimal level of template required for detection by the CPA assay was determined by conducting single crossing amplification assays with serial dilutions of M. tuberculosis bacteria cells. FIG. 12B shows amplicons were observed when as few 4 bacterial cells were present in the amplification reaction, indicating that the CPA assay is able to produce specific amplicons from just a few cells.

In the polymerase chain reaction, the reduction in the background noise of non-specific products derived from mispriming events, or primer-primer interactions is controlled by restricting the number of thermal cycles. In an isothermal amplification reaction, total incubation time will influence the production of specific vs. nonspecific amplicons. Single crossing amplification reactions were incubated from 60 minutes to 210 minutes in the absence of template (FIG. 12C). Non-specific amplicons appeared after 180 minutes with a banding pattern distinct (lane 5) from the pattern obtained after a 60 minute amplification in the presence of the M. tuberculosis DNA template (lane 7). FIG. 12D shows a time course for the production of specific amplicons in a single crossing amplification assay conducted with $10^4$ copies of template DNA. From the intensity of the banding pattern it is apparent that the reaction reaches completion after 28 minutes, while a 60 minute incubation in the absence of template DNA (lane N) does not yield any amplicons.

The specificity of the single crossing amplification reaction was tested using bacterial cells from a variety of mycobacterial species (FIG. 12 E). Amplification products were only observed in the reactions that contained either M. tuberculosis cells (lane 13) or a plasmid template containing M. tuberculosis DNA target region (lane 14), demonstrating that primers used in the assay and the reaction mechanism combine with a high degree of specificity.

The invention is further illustrated by the following non-limiting examples.

EXAMPLES

Example 1

Detection of Chlamydia trachomatis

Since 1990, Chlamydia trachomatis has become the most common pathogen in urinary tract infections supplanting Neisseria gonorrhoeae. Along with the gradually increasing of the Chlamydia trachomatis infection diseases and corresponding complicating diseases, it has become greater threat to the human reproductive health than ever. In 1995, the World Health Organization estimated that there were about 90 million Chlamydia trachomatis patients all over the world, which were only lower that those of HIV infection patients. Therefore, to realize the rapid Chlamydia trachomatis diagnosis has an important significance. The invention patent may be used to rapidly detect the DNA of the Chlamydia trachomatis, whose concrete design on the corresponding primers may be listed as follows: we select the DNA sequences of the Chlamydia trachomatis and the gene fragments for amplification; moreover, the specificity primer may be designed according to the sequences.

The basic components of the amplification reactions are listed below:

| | |
|---|---|
| Displacement primer F | 0.05 µmol |
| Displacement primer R | 0.05 µmol |
| Cross amplification primer F | 0.4 µmol |
| Cross amplification primer R | 0.4 µmol |
| Detection primer F | 0.2 µmol |
| Detection primer R | 0.2 µmol |
| dNTP: | 0.4 mmol |
| Thermopol buffer (10x) | 2 µL |
| MgSO$_4$ | 8 mmol |
| Betaine | 1 mol |
| Bst DNA Ploymerase | 8 units |
| Reaction total volume: | 20 µL |

Displacement primer 1-
(SEQ ID 1)
5'-TTTGCCTTAACCCCACCATT-3'

Displacement primer 2-
(SEQ ID 2)
5'-CCTCTGAAGTCTTAAGCTTG-3'

Cross Amplification primer F-
(SEQ ID 3)
5'-ATTAGTCAGATTTGTTTCCAACTTCCGGAGTTACGAAGA-3'

Cross Amplification primer R-
(SEQ ID 4)
5'-TCCGGAGCGAGTTACGAAGATATTAGTCAGATTTGTTTCCAAC-3'

Detector F-
(SEQ ID 5)
5'-TACAAGAGTACATCGGTCAA-3'

Detector R-
(SEQ ID 6)
5'-GGGAGAAAGAAATGGTAGC-3

Optimization of the reaction time, temperature, primer content and magnesium concentration were investigated. In each case the reactants were held constant except for the parameter being investigated. The reaction time for the amplification reaction were investigating using 66 minutes, 68 minutes, 70 minutes, 72 minutes, 74 minutes, 76 minutes, 78 minutes and 80 minutes. The optimal reaction time appears to be about 80 minutes.

The reaction temperature for the amplification reaction was investigated using 54° C., 56° C., 58° C., 60° C., 62° C., 64° C. and 66° C., the signals are enhanced with increasing reaction temperature up to about 60° C. After about 60° C. the signal decreases thereby indicating that the optimal temperature for the reaction is around 60° C.

The concentration of primers F and R for the amplification reaction were investigated using 0.8 µmol, 0.7 µmol, 0.6

μmol, 0.5 μmol, 0.4 μmol, 0.3 μmol, 0.2 μmol and 0.1 μmol. The optimal concentration of the primers appears to be about 0.4 μmol.

The $Mg^{2+}$ concentration for the amplification reaction was investigated using 10 mmol, 9 mmol, 8 mmol, 7 mmol, 6 mmol and 5 mmol. The optimal $Mg^{2+}$ concentration appears to be about 8 mmol.

Figure 6:
Figure 7:
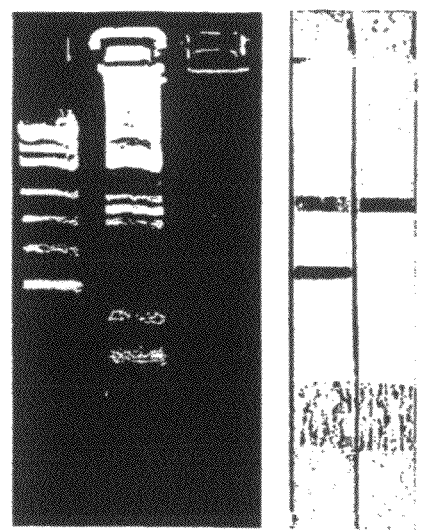
FIG. 7—The results of detecting the amplification products of *Mycobacterium tuberculosis* by testing strips.
Figure 8A:
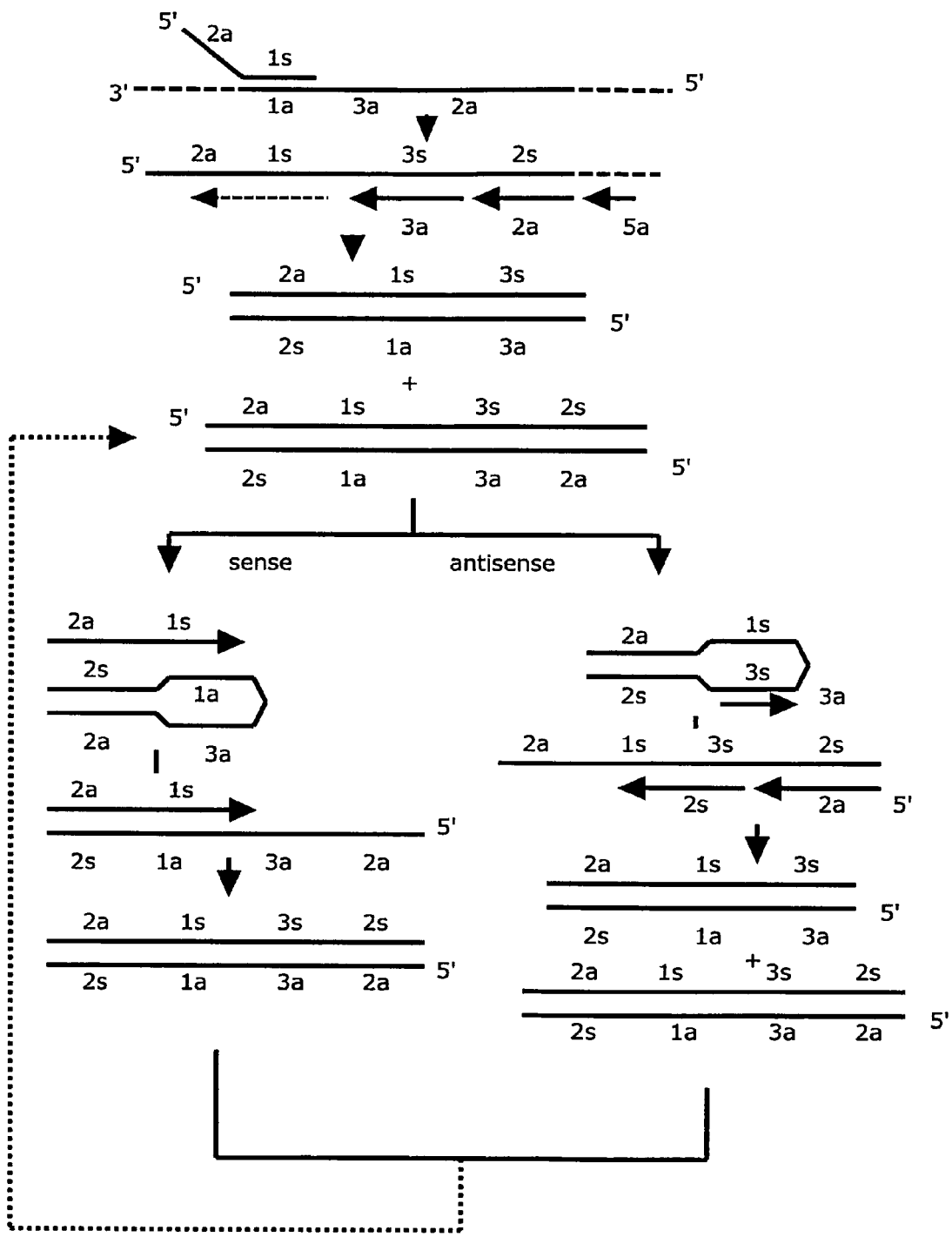
FIG. 8A—A schematic diagram of single crossing amplification
Figure 8E:
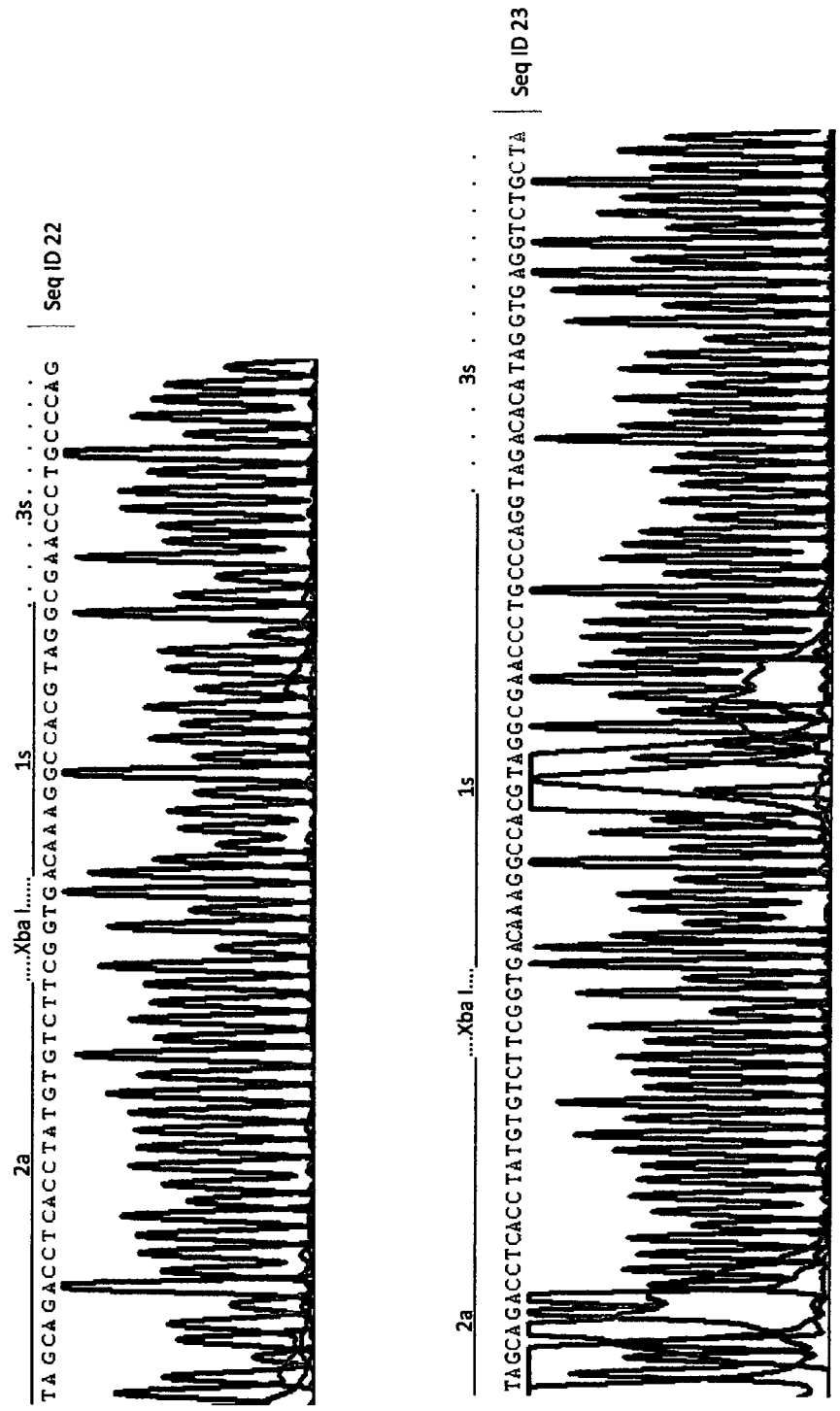
FIG. 8E—Sequencing of CPA amplification products. The 2 bands indicated by arrows at FIG. 8C were excited, cloned and sequenced. The sequences correspond to the final products illustrated in FIG. 8A. The amplification products with higher molecular weight are tandem repeats of these basic units (data not shown).
Figure 9A:
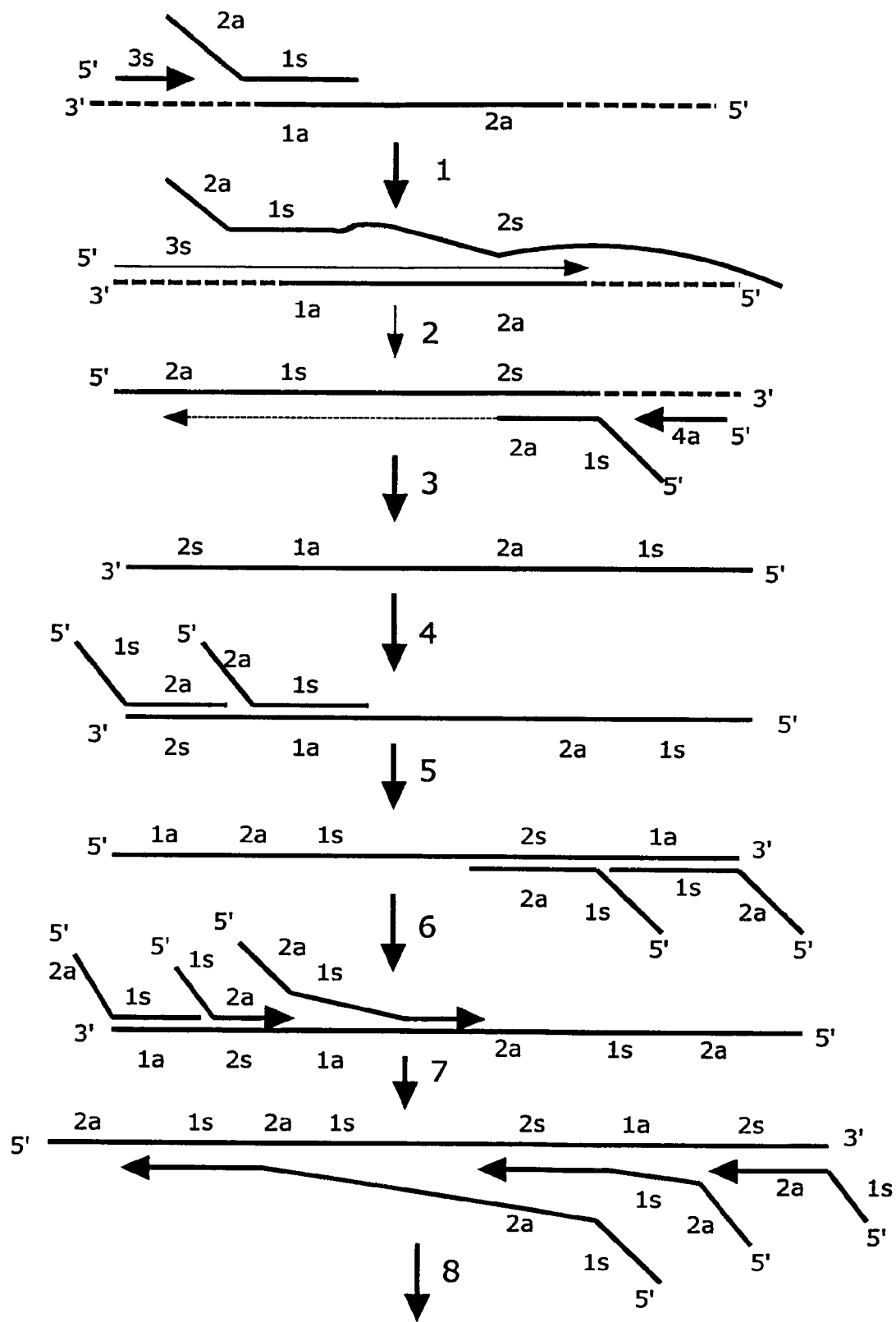
FIG. 9A-A schematic diagram of a mechanism of Cross Priming Amplification (double crossing) High concentration Cross Primer 1s anneal and extend, lower concentration Displace Primer 3s anneal and extend later, displacing the downstream strand. The displaced strand is 5' defined, with a new primer binding site 3) added at the 5' end; Cross Primer 2a anneal and extend, Displace Primer 4a displace the strand. The displaced strand is now 3' and 5' defined, with another primer binding site added at the 5' end, the single stranded DNA may form secondary structures; 4) Both Cross Primer 1s and Cross Primer 2a can anneal to the 3' of the template. The extension product by Cross Primer 2a is elongated by adding another priming site at the 5' end; 5) Similar to step 4 with the other strand; 6), 7) and 8) With each round of extension and displacement, the amplicon is elongated, with repetitive addition of priming sites. The repeated priming sites allow multiple primer annealing and extensions, facilitating the amplification. The repeated sequences also form secondary structures and "branched" DNA, helping the templates stay at single stranded structures. The amplicons at this stage are highly heterozygous, differing in lengths and structures. Multiple DNA synthesis may occur simultaneously on the same template.
Figure 9A:
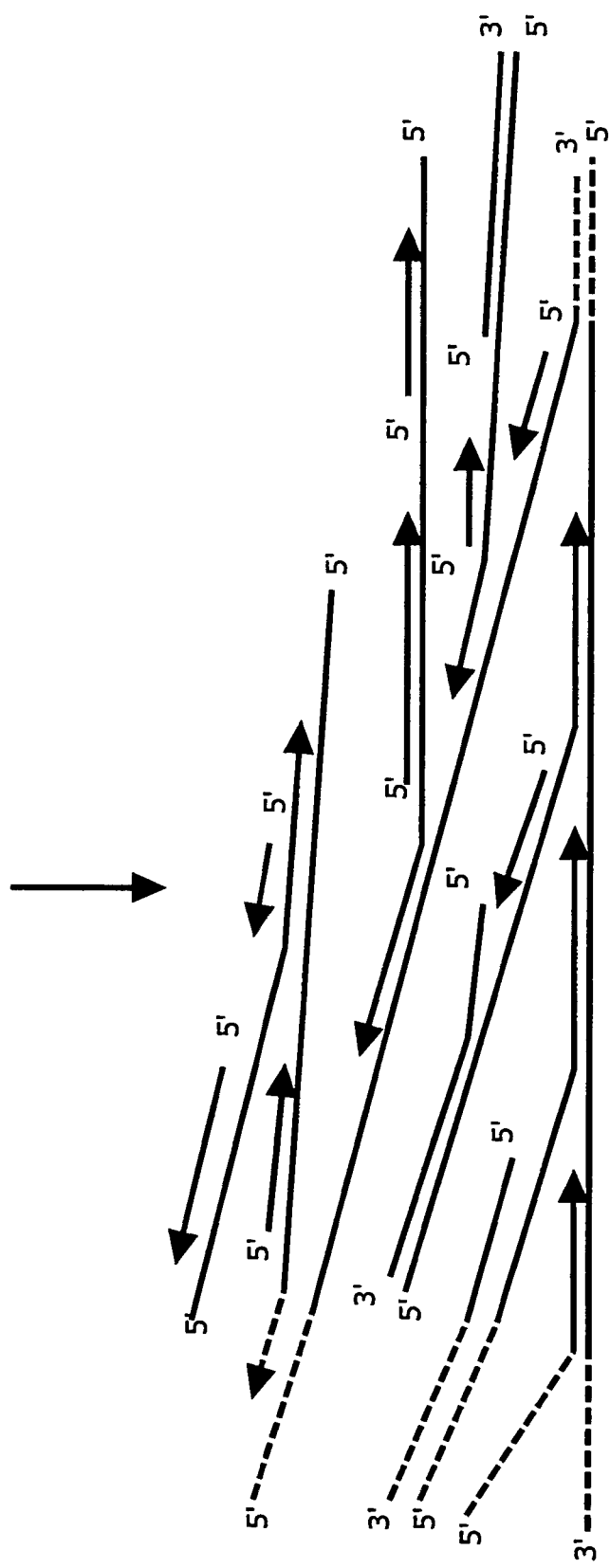
Figure 9C:
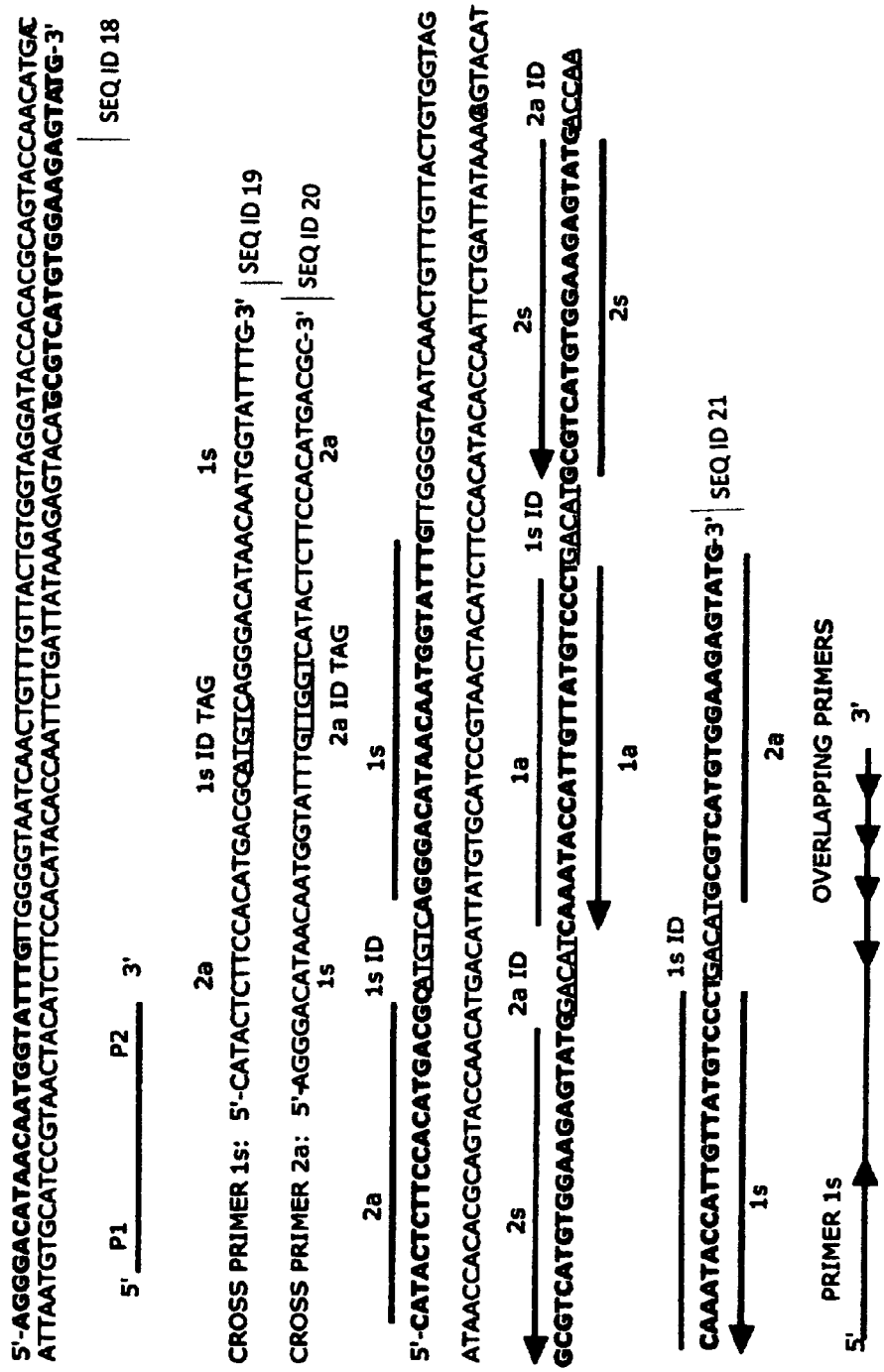
FIG. 9C—HPV target sequence and CPA primer design, displacement primers not shown. The primer tags were designed for identification of each primer location in the sequenced amplicon. The amplification products were cloned and 30 colonies were selected and sequenced. One of CPA amplicon sequences was shown. Note that the cross primers 1s and 2a are overlapping each other.

The results of the detection of the amplification products by using the testing strips is shown in FIG. 6.

Example 2

Detection of *Mycobacterium tuberculosis*

*Mycobacterium tuberculosis* (TB) viral DNA was used as template. The CPA reaction mixture contained five primers F3, B3, F1, F2, BIP, respectively. BIP consisted of B1c sequence complementary to the B1 and the F1 sequence. F1 had labeled Biotin at its 5 end, and F2 labeled was labeled with FitC at its 5' end. Amplification conditions were optimized for temperature, primer and probe concentrations, enzyme units, Mg++ concentration, buffer concentration, and reaction time. The optimized reaction was carried out in a total of 20 μl contained 0.5 μM each BIP, F1 and F2, 0.05 μM F3 and B3, 0.8 mM each dNTP, 1M betaine(sigma), 20 mM Tris-HCl (pH 8.8), 10 mMKCl, 10 mM (NH4)2SO4, 6 mM MgSO4, 0.1% Triton X-100, 8 U Bst DNA polymerase large fragment (New England Biolabs) and the specified amounts of double-stranded target DNA. The mixture was incubated at 66° C. for 1 h, without being heated at 95° C. for 5 min. After incubation, the amplified products were detected by nucleic acid detection strip directly without opening the lid of the PCR tube.

```
                                                       (SEQ ID 7)
AGGACCACGATCGCTCCGGCCACAGCCGTCCCGCCGATCTCGTCCAGCGC

CGCTTCGGACCACCAGCACCTAACCGGCTGTGGGTAGCACCTCACCTATG

TGTCGACCTGGGCAGGGTTCGCCTACGTGGCCTTTGTCACCGACGCCTAC

GCTCGCAGGATCCTGGGCTGGCGGGTCGCTTCCACGATGGCCA

TBMPF2
                                                       (SEQ ID 8)
5'-ACAGCCCGTCCCGCCAT-3'

TBMMRin-5B
                                                       (SEQ ID 9)
5'-TAGCAGACCTCACCTATGTGTC-3'

TBDF-5F2
                                                       (SEQ ID 10)
5'-CTGGGCAGGGTTCGCCT-3'

TBBIP
                                                       (SEQ ID 11)
5'-TAGCAGACCTCACCTATGTGTC-T-TCGGTGACAAAGGCCACGT

TBB3
                                                       (SEQ ID 12)
5'- TCGGTGACAAAGGCCACGT-3'

TBF3
                                                       (SEQ ID 13)
5'-AGGACCACGATCGCTGATC-3'
```

The invention claimed is:

1. A kit for detecting *Mycobacterium tuberculosis* comprising:
   a) a primer set comprising SEQ ID 11 and two or more primers selected from the group of primers consisting of SEQ ID 8, SEQ ID 9, SEQ ID 10 and SEQ ID 17; and
   b) a DNA polymerase.

2. The kit of claim 1 further comprising a detection strip.

3. The kit of claim 2 wherein the detection strip is enclosed in a device that prevents contamination of the sample.

4. The kit of claim 1 wherein the DNA polymerase is Bst DNA polymerase.

* * * * *

SEQUENCE LISTING

<160> NUMBER OF SEQ ID NOS: 23

<210> SEQ ID NO 1
<211> LENGTH: 19
<212> TYPE: DNA
<213> ORGANISM: Chlamydia trachomatis

<400> SEQUENCE: 1
tttgccttaa ccccaccat                                          19

<210> SEQ ID NO 2
<211> LENGTH: 21
<212> TYPE: DNA
<213> ORGANISM: Chlamydia trachomatis

<400> SEQUENCE: 2
cctctgaagt ccttaagctt g                                       21

<210> SEQ ID NO 3
<211> LENGTH: 43
<212> TYPE: DNA
<213> ORGANISM: Chlamydia trachomatis

<400> SEQUENCE: 3
attagtcaga tttgtttcca acttccggag cgagttacga aga               43

<210> SEQ ID NO 4
<211> LENGTH: 43
<212> TYPE: DNA
<213> ORGANISM: Chlamydia trachomatis

<400> SEQUENCE: 4

```
tccggagcga gttacgaaga tattagtcag atttgtttcc aac          43
```

<210> SEQ ID NO 5
<211> LENGTH: 20
<212> TYPE: DNA
<213> ORGANISM: Chlamydia trachomatis

<400> SEQUENCE: 5

```
tacaagagta catcggtcaa                                    20
```

<210> SEQ ID NO 6
<211> LENGTH: 19
<212> TYPE: DNA
<213> ORGANISM: Chlamydia trachomatis

<400> SEQUENCE: 6

```
gggagaaaga aatggtagc                                     19
```

<210> SEQ ID NO 7
<211> LENGTH: 193
<212> TYPE: DNA
<213> ORGANISM: Mycobacterium tuberculosis

<400> SEQUENCE: 7

```
aggaccacga tcgctccggc cacagccgtc ccgccgatct cgtccagcgc cgcttcggac    60
caccagcacc taaccggctg tgggtagcac ctcacctatg tgtcgacctg ggcagggttc   120
gcctacgtgg cctttgtcac cgacgcctac gctcgcagga tcctgggctg gcgggtcgct   180
tccacgatgg caa                                                      193
```

<210> SEQ ID NO 8
<211> LENGTH: 18
<212> TYPE: DNA
<213> ORGANISM: Mycobacterium tuberculosis

<400> SEQUENCE: 8

```
acagcccgtc ccgccgat                                      18
```

<210> SEQ ID NO 9
<211> LENGTH: 24
<212> TYPE: DNA
<213> ORGANISM: Mycobacterium tuberculosis

<400> SEQUENCE: 9

```
tagcagacct cacctatgtg tgtc                               24
```

<210> SEQ ID NO 10
<211> LENGTH: 17
<212> TYPE: DNA
<213> ORGANISM: Mycobacterium tuberculosis

<400> SEQUENCE: 10

```
ctgggcaggg ttcgcct                                       17
```

<210> SEQ ID NO 11
<211> LENGTH: 49
<212> TYPE: DNA
<213> ORGANISM: Mycobacterium tuberculosis

<400> SEQUENCE: 11

```
tagcagacct cacctatgtg tgtctctaga tcggtgacaa aggccacgt    49
```

```
<210> SEQ ID NO 12
<211> LENGTH: 19
<212> TYPE: DNA
<213> ORGANISM: Mycobacterium tuberculosis

<400> SEQUENCE: 12
tcggtgacaa aggccacgt                                                      19

<210> SEQ ID NO 13
<211> LENGTH: 19
<212> TYPE: DNA
<213> ORGANISM: Mycobacterium tuberculosis

<400> SEQUENCE: 13
aggaccacga tcgctgatc                                                      19

<210> SEQ ID NO 14
<211> LENGTH: 207
<212> TYPE: DNA
<213> ORGANISM: Chlamydia trachomatis

<400> SEQUENCE: 14
tttgccttaa ccccaccatt tttccggagc gagttacgaa gacaaaacct cttcgttgac         60
cgatgtactc ttgtagaaag tcataaacct tctgaggata agttataata atcctctttt        120
ctgtctgacg gttcttaagc tgggagaaag aaatggtagc ttgttggaaa caaatctgac        180
taatctccaa gcttaagact tcagagg                                            207

<210> SEQ ID NO 15
<211> LENGTH: 206
<212> TYPE: DNA
<213> ORGANISM: Chlamydia trachomatis

<400> SEQUENCE: 15
cctctgaagt cttaagcttg gagattagtc agatttgttt ccaacaagct accatttctt         60
tctcccagct taagaaccgt cagacagaaa agaggattat tataacttat cctcagaagt        120
ttatgacttt ctacaagagt acatcggtca acgaagaggt tttgtcttcg taactcgctc        180
cggaaaaatg gtggggttaa ggcaaa                                             206

<210> SEQ ID NO 16
<211> LENGTH: 178
<212> TYPE: DNA
<213> ORGANISM: Mycobacterium tuberculosis

<400> SEQUENCE: 16
gccatcgtgg aagcgcccccg ccagcccagg atcctgcgac gtaggcgctc ggtgacaaag        60
gccacgtagg cgaaccctgc ccaggtcgac ataggtga ggtctgctaa ccacagccgg          120
ttaggtgctg gtggtccgaa gcggcgctgg acgagatcgg cgggacggga cgggctgt         178

<210> SEQ ID NO 17
<211> LENGTH: 16
<212> TYPE: DNA
<213> ORGANISM: Mycobacterium tuberculosis

<400> SEQUENCE: 17
gccatcgtgg aagcga                                                         16

<210> SEQ ID NO 18
<211> LENGTH: 158
<212> TYPE: DNA
<213> ORGANISM: Human papillomavirus type 10
```

```
<400> SEQUENCE: 18
agggacataa caatatttgt tggggtaatc aactgtttgt tactgtggta ggataccaca    60
cgcagtacca acatgacatt aatgtgcatc cgtaactaca tcttccacat acaccaattc   120
tgattataaa gagtacatgc gtcatgtgga agagtatg                          158

<210> SEQ ID NO 19
<211> LENGTH: 48
<212> TYPE: DNA
<213> ORGANISM: Human papillomavirus type 10

<400> SEQUENCE: 19
catactcttc cacatgacgc atgtcaggga cataacaatg gtattttg                48

<210> SEQ ID NO 20
<211> LENGTH: 48
<212> TYPE: DNA
<213> ORGANISM: Human papillomavirus type 10

<400> SEQUENCE: 20
aggggacata acaatggtat ttgttggtca tactcctcca catgacgc                48

<210> SEQ ID NO 21
<211> LENGTH: 292
<212> TYPE: DNA
<213> ORGANISM: Human papillomavirus type 10

<400> SEQUENCE: 21
catactcttc cacatgacgc atgtcaggga cataacaatg gtattttgtt ggggtaatca    60
actgtttgtt actgtggtag ataaccacac gcagtaccaa catgacatta tgtgcatccg   120
taactacatc ttccacatac accaattctg aatataaaga gtacatgcgt catgtggaag   180
agtatggaca tcaaatacca ttgttatgtc cctgacatgt gtcatgtgga agagtatgac   240
caacaaatac cattgttatg tccctgacat gcgtcatgtg gaagagagta tg          292

<210> SEQ ID NO 22
<211> LENGTH: 59
<212> TYPE: DNA
<213> ORGANISM: Mycobacterium tuberculosis

<400> SEQUENCE: 22
tagcagacct cacctatgtg tcttcggtga caaaggccac gtaggcgaac cctgcccag     59

<210> SEQ ID NO 23
<211> LENGTH: 84
<212> TYPE: DNA
<213> ORGANISM: Mycobacterium tuberculosis

<400> SEQUENCE: 23
tagcagacct cacctatgtg tcttcggtga caaaggccac gtaggcgaac cctgcccagg    60
tagacacata ggtgaggtct gcta                                          84
```